(12) United States Patent
Hoffman

(10) Patent No.: US 6,316,437 B1
(45) Date of Patent: Nov. 13, 2001

(54) SPIROHYDANTOIN COMPOUNDS AND USES THEREOF

(75) Inventor: Jacob M. Hoffman, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/671,417

(22) Filed: Sep. 27, 2000

Related U.S. Application Data

(60) Provisional application No. 60/157,205, filed on Sep. 30, 1999.

(51) Int. Cl.$^7$ .......................... A61K 31/44; A01N 43/40; C07D 223/14; C07D 211/80; C07D 235/00

(52) U.S. Cl. .................... 514/212.02; 514/278; 514/323; 514/324; 514/325; 514/326; 514/431; 514/450; 540/543; 546/18; 546/192; 546/196; 546/210; 548/300.7; 548/301.1

(58) Field of Search .............................. 514/212.02, 278, 514/323, 324, 325, 326, 431, 450; 540/543; 546/18, 192, 196, 210; 548/300.7, 301.1

(56) References Cited

U.S. PATENT DOCUMENTS

| | | |
|---|---|---|
| 4,117,230 | 9/1978 | Sarges . |
| 4,147,795 | 4/1979 | Sarges . |
| 4,209,630 | 6/1980 | Sarges . |
| 4,210,756 | 7/1980 | Sarges . |
| 4,258,054 | 3/1981 | Sarges . |
| 4,282,229 | 8/1981 | Sarges . |
| 4,537,892 | 8/1985 | York, Jr. . |
| 4,556,670 | 12/1985 | Lipinski . |
| 4,864,028 | 9/1989 | York, Jr. . |
| 5,070,100 | 12/1991 | York, Jr. . |
| 5,153,211 | 10/1992 | York, Jr. . |

FOREIGN PATENT DOCUMENTS

| | | |
|---|---|---|
| 27 46 244 | 4/1978 | (DE) . |
| 35 03 074 | 8/1985 | (DE) . |
| 0 137 333 | 4/1985 | (EP) . |
| 0 159 143 | 10/1985 | (EP) . |
| 0 204 597 | 12/1986 | (EP) . |
| 0 748 800 | 12/1996 | (EP) . |
| 2 155 466 A | 9/1985 | (GB) . |
| 59-116274 | 7/1984 | (JP) . |
| 62026282 | 2/1987 | (JP) . |
| WO 92/00073 | 1/1992 | (WO) . |
| WO 92/16213 | 10/1992 | (WO) . |
| WO 94/08040 | 4/1994 | (WO) . |
| WO 94/10989 | 5/1994 | (WO) . |
| WO 94/22829 | 10/1994 | (WO) . |
| WO 96/14846 | 5/1996 | (WO) . |
| WO 96/40135 | 12/1996 | (WO) . |
| WO 97/17969 | 5/1997 | (WO) . |
| WO 97/42956 | 11/1997 | (WO) . |
| WO 98/57632 | 12/1998 | (WO) . |
| WO 98/57638 | 12/1998 | (WO) . |
| WO 98/57639 | 12/1998 | (WO) . |
| WO 98/57640 | 12/1998 | (WO) . |
| WO 98/57641 | 12/1998 | (WO) . |
| WO 98/57642 | 12/1998 | (WO) . |
| WO 98/57940 | 12/1998 | (WO) . |

OTHER PUBLICATIONS

Watson & Girdlestone, "TiPS in nomenclature", Receptor & Ion Channel Nomenclature Supplement, 1995.

Michel, et al., "Classification of Alpha 1 adrenoceptor subtypes", Naunyn–Schmiedeberg's Arch. Pharmacol., 352:1–10; 1995.

Sarges, et al., " SpironHydantoin Aldose Reductase Inhibitors", J. Med. Chem., 31(1): 230–243; 1988.

Griffin, et al., "Effects of Two New Aldose Reductase Inhibitors, AL–1567 and Al–1576 in Diabetic Rats", Metab., Clin. Exp., 36(5): 486–490; 1987.

Matsukura, et al.," Syntheis and Antiarrhthimic Activity of 2,2–Dialkyl–1'–(N–substituted aminoalkyl)spiro–[chroman–4,4'–imidazolidine]–2',5'–diones", Japan. Chem. Pharm. Bull.; 40: 1823–1827; 1992.

Gonzalez, et al., "Heterocyclic spiro derivatives. XI Some 3'–dialkylaminoalkyl derivitives of indano–1–,indano–2–, and fluoreneo–9–spiro–5'hydantoins", An Quim, 74(7–8): 1090–1092; 1978 (SciFinder Abstract).

Coffey, S., "Heterocyclic Compounds", Rodd's Chemistry of Carbon Compounds, vol. IV, Part F: pp. 212–225; 1976.

Elderfield, R. C., "Three–, Four–, Five–, and Six–Membered Monocyclic Compounds Containing One O, N and S Atom", Heterocyclic Compounds, vol. 1: pp. v, 630–663; 1950.

*Primary Examiner*—Mukund J. Shah
*Assistant Examiner*—Tamthom N. Truong
(74) *Attorney, Agent, or Firm*—Baerbel R. Brown; Catherine D. Fitch; Kenneth R. Walton

(57) ABSTRACT

Spirohydantoin compounds and their pharmaceutically acceptable salts are disclosed. The synthesis of these compounds and their use as alpha 1a adrenergic receptor antagonists is also described. One application of these compounds is in the treatment of benign prostatic hyperplasia. These compounds are typically selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

30 Claims, No Drawings

SPIROHYDANTOIN COMPOUNDS AND USES THEREOF

This application claims the benefit of U.S. Provisional Application No. 60/157,205 filed Sep. 30, 1999, the disclosure of which is hereby incorporated by reference in its entirety.

FIELD OF THE INVENTION

This invention relates to spirohydantoin compounds and pharmaceutically acceptable salts thereof, their synthesis, and their use as alpha 1a adrenoceptor antagonists. The spirohydantoin compounds of the present invention include, but are not limited to, compounds having (1-azacycloalkyl) alkyl, azacycloalkylaminoalkyl, or cycloalkylaminoalkyl groups as side chains on a hydantoin ring nitrogen. The compounds of the present invention are useful for treating benign prostatic hyperplasia (BPH).

References are made throughout this application to various publications, the disclosures of which are hereby incorporated by reference in their entireties, in order to more fully describe the state of the all to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Michel et al., *Naunyn-Schmiedeberg's Arch. Pharmacol.* (1995), 352: 1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-α reductase, which converts testosterone into 5α-dihydrotestosterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype was reported. In addition, in WO 92/16213, combinations of 5α reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The relatively recent cloning of the human alpha 1a adrenergic receptor (ATCC CRL 11140) and the use of a screening assay utilizing the cloned human alpha 1a receptor has enabled identification of compounds which specifically interact with the human alpha 1a adrenergic receptor. For further description, see WO 94/08040 and WO 94/10989. As disclosed in the instant patent disclosure, a cloned human alpha 1a adrenergic receptor and a method for identifying compounds which bind the human alpha 1a receptor have made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, selective alpha 1a antagonists with weak calcium channel antagonistic activity and which are further described to be anticipated as useful for treating BPH. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use as selective alpha 1a antagonists. Yet another example is EP 748800, which discloses, inter alia, certain arylpiperazinylpropyl substituted pyrimidinediones useful as alpha 1 adrenoceptor antagonists. Still other alpha 1a selective antagonist compounds are disclosed in WO 98/57632, WO 98/57638, WO 98/57639, WO 98/57640, WO 98/57641, WO 98/57642, and WO 98/57940.

Certain spirohydantoin compounds have been disclosed to be aldose reductase inhibitors and have been proposed for use in treating complications of diabetes mellitus. Sarges et al., *J. Med. Chem.* 1988, 30: 230–243 and U.S. Pat. No. 4,147,795 disclose, inter alia, certain spiro[benzopyran-, benzothiopyran-, benzothiodioxopyran-, and benzothiooxopyran-imidazolidinedione]s as aldose reductase inhibitors. Griffin et al., *Metab., Clin. Exp.* 1987, 36: 486–490 discloses two spiro[fluoro-9H-fluorene-imidazolinedione]s to be aldose reductase inhibitors and proposes their use as therapeutic agents in human diabetics.

Spirohydantoin compounds have also been proposed for use antiarrhythmic agents. Matsukura et al., *Japan. Chem. Pharm. Bull.* 1992, 40: 1823–27 and JP 62-026282 disclose spiro[chroman4,4'-imidazolidine]-2',5'-dione derivatives as antiarrythmics, including 1'-((4-phenylpiperidin-1-yl)alkyl) spiro[chroman4,4'-imidazoline]-2',5'-dione.

The instant patent specification discloses novel spirohydantoin compounds which bind to the human alpha 1a receptor. These compounds are further tested for binding to other human alpha 1 receptor subtypes, as well as counter-screened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides spirohydantoin compounds and pharmaceutically acceptable salts thereof for the treatment of urinary obstruction caused by benign prostatic hyperplasia (BPH). The compounds antagonize the human alpha 1a adrenergic receptor at nanomolar and subnanomolar concentrations, while exhibiting lower affinity for the alpha 1d and alpha 1b human adrenergic receptors and many other G-protein coupled receptors. This invention can have the advantage over non-selective alpha 1 adrenoceptor antagonists of reduced side effects related to peripheral adrenergic blockade. Such side effects include hypotension, syncope, lethargy, etc.

More particularly, the present invention is a compound of formula (I):

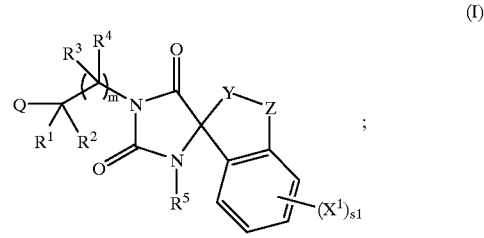

(I)

wherein Q is

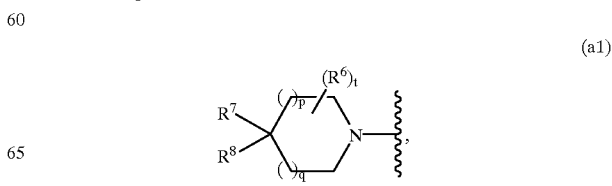

(a1)

-continued

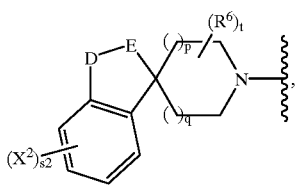
(a2)

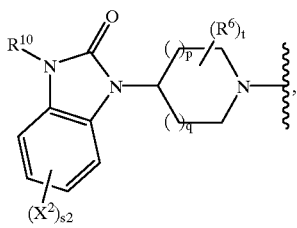
(a3)

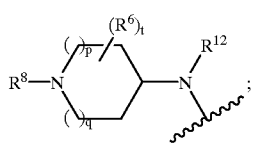
(a4)

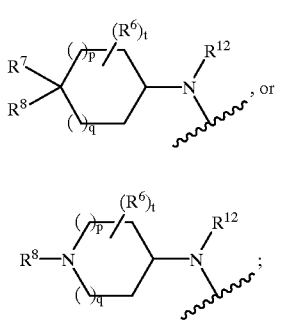
(a5)

$R^1$, $R^2$, $R^3$ and $R^4$ are each independently selected from hydrogen, fluorine, $C_1$–$C_6$ alkyl, and $C_3$–$C_8$ cycloalkyl;

$R^5$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $(CH_2)_{1-4}CO_2R^d$, $(CH_2)_{1-4}C(=O)N(R^d)_2$, $C_2$–$C_8$ alkoxyalkyl, or fluorinated $C_2$–$C_8$ alkoxyalkyl;

each $R^6$ is a substituent connected to a ring atom other than $C(R^7R^8)$, spiro substituted carbon, or N and is independently hydrogen or $C_1$–$C_4$ alkyl;

$R^7$ is hydrogen, cyano, hydroxy, $CO_2R^d$, $CON(R^d)_2$, aryl, or substituted aryl; wherein each of the substituents on substituted aryl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^8$ is aryl, substituted aryl, heteroaryl, or substituted heteroaryl; wherein each of the substituents on substituted aryl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $(CH_2)_{0-4}C(=O)N(R^d)_2$, $(CH_2)_{0-4}SO_2R^d$, $C_2$–$C_8$ alkoxyalkyl, or fluorinated $C_2$–$C_8$ alkoxyalkyl; and wherein each of the substituents on substituted heteroaryl is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^{10}$ is hydrogen, $C_1$–$C_6$ alkyl, fluorinated $C_1$–$C_6$ alkyl, $C_3$–$C_8$ cycloalkyl, or fluorinated $C_3$–$C_8$ cycloalkyl;

$R^{12}$ is hydrogen or $C_1$–$C_4$ alkyl;

each $X^1$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

Y is $C(R^a)=C(R^b)$, $C(R^aR^b)—C(R^a)=C(R^b)$, $C(R^a)=C(R^b)—C(R^aR^b)$, $[C(R^aR^b)]_{1-3}$, or

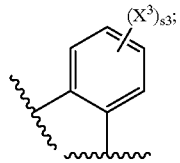

Z is absent, $C(R^aR^b)$, O, S, SO, $SO_2$, or $N(R^c)$; provided that (i) when Z is absent, Y is $C(R^a)=C(R^b)$, $C(R^aR^b)—C(R^a)=C(R^b)$, $C(R^a)=C(R^b)—C(R^aR^b)$, or

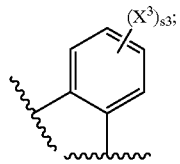

and (ii) when Z is $C(R^aR^b)$, O, S, SO, $SO_2$, or $N(R^c)$, Y is $[C(R^aR^b)]_{1-3}$ or

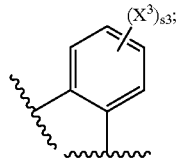

D is absent, $[C(R^aR^b)]_{1-4}$, $O[C(R^aR^b)]_{1-2}$, $[C(R^aR^b)]_{1-2}O$, $C(R^a)=C(R^b)$, $C(R^aR^b)—C(R^a)=C(R^b)$, or $C(R^a)=C(R^b)—C(R^aR^b)$;

E is absent, $C(=O)$, $C(=O)O$, $N(SO_2R^c)C(R^aR^b)$, $N(R^c)C(=O)$, or $N(R^c)C(=O)O$, provided that (i) when E is absent, D is $[C(R^aR^b)]_{2-4}$, $O[C(R^aR^b)]_{1-2}$, $[C(R^aR^b)]_{1-2}O$, $C(R^a)=C(R^b)$, $C(R^aR^b)—C(R^a)=C(R^b)$, or $C(R^a)=C(R^b)—C(R^aR^b)$; (ii) when Z is $C(=O)$ or $C(=O)O$, D is $C(R^aR^b)$ or $C(R^aR^b)C(R^aR^b)$; and (iii) when E is $N(SO_2R^c)C(R^aR^b)$, $N(R^c)C(=O)$ or $N(R^c)C(=O)O$, D is absent or $C(R^aR^b)$;

each $X^2$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

each $X^3$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

$R^a$ and $R^b$ are each independently hydrogen, $C_1$–$C_4$ alkyl, and fluorinated $C_1$–$C_4$ alkyl;

$R^c$ is hydrogen, $C_1$–$C_4$ alkyl, or fluorinated $C_1$–$C_4$ alkyl;
$R^d$ is hydrogen, $C_1$–$C_6$ alkyl, or fluorinated $C_1$–$C_6$ alkyl;
m is an integer from 1 to 4;
p and q are each independently integers from 0 to 3;
s1 is an integer from 0 to 4;
s2 is an integer from 0 to 4;
s3 is an integer from 0 to 4; and
t is an integer from 0 to 4;
and provided that when Q is of formula (a1), Z is O, Y is $[C(R^aR^b)]_{1-3}$, and $R^8$ is aryl, then $R^7$ is cyano, $CO_2R^d$, $CON(R^d)_2$, or substituted aryl;
or a pharmaceutically acceptable salt thereof.

The present invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes spirohydantoin compounds of Formula (I) above. These compounds and their pharmaceutically acceptable salts are useful as alpha 1a antagonists.

An aspect of the present invention is a compound of Formula (I), wherein the compound is a (+)-enantiomer; or a pharmaceutically acceptable salt thereof. Another aspect of the present invention is a compound of Formula (I), wherein the compound is a (−)-enantiomer; or a pharmaceutically acceptable salt thereof.

A first embodiment of the present invention is a compound of Formula (I), wherein
one of $R^1$ and $R^2$ is hydrogen or fluorine and the other of $R^1$ and $R^2$ is hydrogen, fluorine, $C_1$–$C_6$ alkyl, or $C_3$–$C_8$ cycloalkyl;
one of $R^3$ and $R^4$ is hydrogen or fluorine and the other of $R^3$ and $R^4$ is hydrogen, fluorine, $C_1$–$C_6$ alkyl, or $C_3$–$C_8$ cycloalkyl;
$R^5$ is hydrogen, $C_1$–$C_4$ alkyl, fluorinated $C_1$–$C_4$ alkyl, $C_3$–$C_6$ cycloalkyl, fluorinated $C_3$–$C_6$ cycloalkyl, $(CH_2)_{1-2}CO_2R^d$, $(CH_2)_{1-2}C(=O)N(R^d)_2$, $C_2$–$C_8$ alkoxyalkyl, or fluorinated $C_2$–$C_8$ alkoxyalkyl;
$R^7$ is hydrogen, cyano, hydroxy, $CO_2R^d$, $CON(R^d)_2$, phenyl, or mono- or di- or tri-substituted phenyl;
$R^8$ is phenyl, naphthyl, pyridyl, pyrazinyl, thienyl, furanyl, or mono- or di- or tri-substituted phenyl, naphthyl, pyridyl, pyrazinyl, thienyl, or furanyl;
$R^d$ is hydrogen, $C_1$–$C_4$ alkyl, or $(CH_2)_{0-4}CF_3$;
m is an integer from 1 to 3;
p and q are each integers from 0 to 3, provided that the sum of p and q is an integer less than or equal to 3;
s1 is an integer from 0 to 3;
s2 is an integer from 0 to 2;
s3 is an integer from 0 to 2;
t is an integer from 0 to 2;
and all other variables are as originally defined;
and provided that when Q is of formula (a1), Z is O, Y is $[C(R^aR^b)]_{1-3}$, and $R^8$ is phenyl, then $R^7$ is cyano, $CO_2R^d$, $CON(R^d)_2$, or mono- or di- or tri-substituted phenyl;
or a pharmaceutically acceptable salt thereof.

A second embodiment of the present invention is a compound of Formula (I), wherein Q is

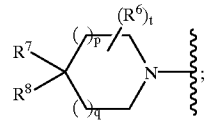

and all other variables are as defined in the first embodiment;
and provided that when Z is O, Y is $[C(R^aR^b)]_{1-3}$, and $R^8$ is phenyl, then $R^7$ is cyano, $CO_2R^d$, $CON(R^d)_2$, or mono- or di- or tri-substituted phenyl;
or a pharmaceutically acceptable salt thereof.

A first class of the present invention is a compound of Formula (II):

(II)

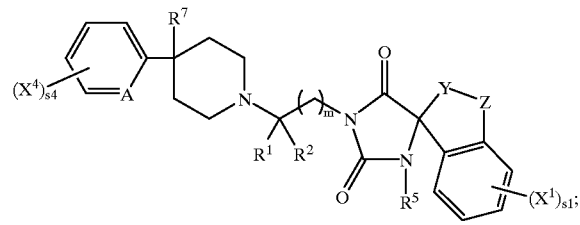

wherein
A is N or $CX^4$;
one of $R^1$ and $R^2$ is hydrogen and the other of $R^1$ and $R^2$ is hydrogen, methyl, or ethyl;
$R^5$ is hydrogen, methyl, ethyl, $CH_2OCH_3$, $CH_2OCH_2CH_3$, $CH_2CO_2CH_3$, or $CH_2CO_2CH_2CH_3$;
$R^7$ is hydrogen, hydroxy, cyano, $CO_2R^d$, $CON(R^d)_2$, phenyl, or mono- or di-substituted phenyl; wherein each of the substituents on substituted phenyl is independently halogen, cyano, hydroxy, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;
Y is $C(R^a)=C(R^b)$, $[C(R^aR^b)]_{1-3}$, or

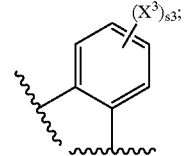

Z is absent, $C(R^aR^b)$, O, S, SO, $SO_2$, or $N(R^c)$; provided that (i) when Z is absent, Y is $C(R^a)=C(R^b)$ or

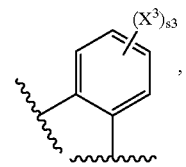

and (ii) when Z is $C(R^aR^b)$, O, S, SO, $SO_2$, or $N(R^c)$, Y is $[C(R^aR^b)]_{1-3}$;
each $X^1$ is independently hydrogen, halogen, cyano, $C_1$–$C_4$ alkyl, $(CH_2)_{0-4}OCF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each X³ is independently hydrogen, halogen, cyano, C₁–C₄ alkyl, (CH₂)₀₋₄CF₃, C₁–C₄ alkoxy, OCF₃, (CH₂)₀₋₄CO₂Rᵈ, (CH₂)₁₋₄OCH₃, or (CH₂)₁₋₄OCF₃;

each X⁴ is independently hydrogen, halogen, cyano, C₁–C₄ alkyl, (CH₂)₀₋₄CF₃, C₁–C₄ alkoxy, OCF₃, (CH₂)₀₋₄CO₂Rᵈ, (CH₂)₁₋₄OCH₃, or (CH₂)₁₋₄OCF₃;

Rᵃ and Rᵇ are each independently hydrogen, C₁–C₄ alkyl, and fluorinated C₁–C₄ alkyl;

Rᶜ is hydrogen, C₁–C₄ alkyl, or fluorinated C₁–C₄ alkyl;

Rᵈ is hydrogen, methyl, ethyl, or CF₃;

m is an integer equal to 2 or 3;

s1 is an integer from 0 to 3;

s3 is an integer from 0 to 2; and s4 is an integer from 0 to 3;

and provided that when Z is O and

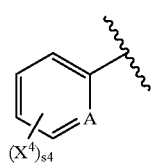

is phenyl, then R⁷ is cyano, CO₂Rᵈ, CON(Rᵈ)₂, or mono- or di- or tri-substituted phenyl;

or a pharmaceutically acceptable salt thereof.

A subclass of the first class is a compound of Formula (III):

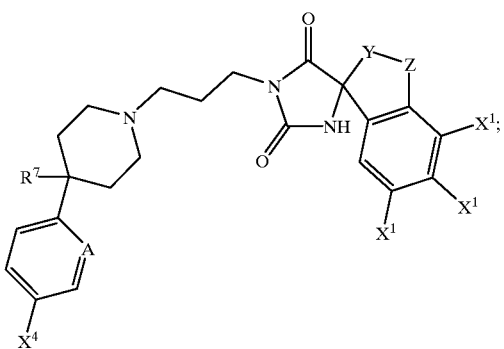

(III)

wherein

A is N or CX⁴;

R⁷ is hydrogen or cyano;

Y is CH=CH, (CH₂)₁₋₃, or

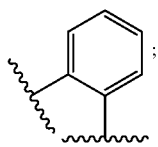

;

Z is absent, CH₂, O, S, SO, or SO₂; provided that (i) when Z is absent, Y is CH=CH or

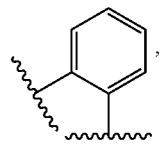

, and (ii) when Z is CH₂, O, S, SO, or SO₂, Y is (CH₂)₁₋₃;

each X¹ is independently hydrogen, fluorine, chlorine, cyano, methyl, ethyl, methoxy, ethoxy, CF₃, or OCF₃; and each X⁴ is independently hydrogen, fluorine, chlorine, cyano, methyl, ethyl, methoxy, ethoxy, CF₃, or OCF₃;

and provided that when Z is O and

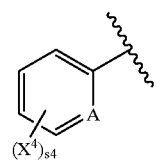

is phenyl, then R⁷ is cyano;

or a pharmaceutically acceptable salt thereof.

Exemplary of compounds embraced by the first embodiment are compounds selected from the group consisting of 1-{3-[4-(4-fluorophenyl)piperidin-1-yl]butyl}-5'-chloro-spiro[imidazolidine-4,1'indan]-2,5-dione;

(+/−)-1-{3-[4-(2-cyano-4-fluorophenyl)piperidin-1-yl]propyl}-5'-fluoro-spiro[imidazolidine-4,1'indan]-2,5-dione;

(+)-1-{3-[4-(2-cyano-4-fluorophenyl)piperidin-1-yl]propyl}-5'-fluoro-spiro[imidazolidine-4,1'indan]-2,5-dione;

(−)-1-{3-[4-(2-cyano-4-fluorophenyl)piperidin-1-yl]propyl}-5'-fluoro-spiro[imidazolidine-4,1'indan]-2,5-dione;

(+/−)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione;

(+)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione;

(−)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione;

(+/−)-1-{3-[4-(4-fluorophenyl)piperidin-1-yl]propyl}-5'-fluoro-spiro[imidazolidine-4,1'indan]-2,5-dione;

(+/−)-1-{3-[4-cyano-4-phenyl-piperidin-1-yl]propyl}-5'-fluoro-spiro[imidazolidine-4,1'indan]-2,5-dione;

(+)-1-{3-[4-cyano-4-phenyl-piperidin-1-yl]propyl}-5'-fluoro-spiro[imidazolidine-4,1'indan]-2,5-dione;

(−)-1-{3-[4-cyano-4-phenyl-piperidin-1-yl]propyl}-5'-fluoro-spiro[imidazolidine-4,1'indan]-2,5-dione;

(+/−)-1-{3-[4-(4-cyano-4-(2-cyanophenyl))piperidin-1-yl]propyl}-5'-fluoro-spiro[imidazolidine-4,1'indan]-2,5-dione;

(+/−)-1-{3-[4-cyano-4-phenyl-piperidin-1-yl]propyl}-6'-fluoro-spiro[imidazolidine-4,1'indan]-2,5-dione;

(+/−)-1-{3-[4-(4-fluoro-2-cyanophenyl)piperidin-1-yl]propyl}-5',6'-difluoro-spiro[imidazolidine-4,1'indan]-2,5-dione;

(+)-1-{3-[4-(4-fluoro-2-cyanophenyl)piperidin-1-yl]propyl}-5',6'-difluoro-spiro[imidazolidine4,1'indan]-2,5-dione;

(−)-1-{3-[4-(4-fluoro-2-cyanophenyl)piperidin-1-yl]propyl}-5',6'-difluoro-spiro[imidazolidine-4,1'indan]-2,5-dione;

(+/−)-1-{3-[4-(4-fluorophenyl)piperidin-1-yl]propyl}-5'-chloro-spiro[imidazolidine-4,1'indan]-2,5-dione;

(+/−)-1-{3-[4-(4-fluoro-2-cyanophenyl)piperidin-1-yl]propyl}-5'-chloro-spiro[imidazolidine-4,1'indan]-2,5-dione;

(+)-1-{3-[4-(4-fluoro-2-cyanophenyl)piperidin-1-yl]propyl}-5'-chloro-spiro[imidazolidine-4,1'indan]-2,5-dione;

(−)-1-{3-[4-(4-fluoro-2-cyanophenyl)piperidin-1-yl]propyl}-5'-chloro-spiro[imidazolidine-4,1'indan]-2,5-dione;

(+/−)-1-{3-[4-(2-pyridinyl)piperidin-1-yl]propyl}-5'-chloro-spiro[imidazolidine-4,1'indan]-2,5-dione;

(+/−)-1-{3-[4-(4-fluoro-2-cyanophenyl)piperidin-1-yl]propyl}-5'-methyl-spiro[imidazolidine-4,1'indan]-2,5-dione;

(+)-1-{3-[4-(4-fluoro-2-cyanophenyl)piperidin-1-yl]propyl}-5'-methyl-spiro[imidazolidine-4,1'indan]-2,5-dione;

(−)-1-{3-[4-(4-fluoro-2-cyanophenyl)piperidin-1-yl]propyl}-5'-methyl-spiro[imidazolidine4,1'indan]-2,5-dione;

(+/−)-1-{3-[4-cyano-4-phenyl-piperidin-1-yl]propyl}-3-fluoro-spiro[9H-fluorene-9,4'-imidazolidine]-2',5'-dione;

(+/−)-1'-{3-[4-(4-fluorophenyl)piperidin-1-yl]propyl}-7-fluoro-2,3-dihydro-spiro[4H-1-benzopyran-4,4'-imidazolidine]-2',5'-dione;

(+)-1'-{3-[4-(4-fluorophenyl)piperidin-1-yl]propyl}-7-fluoro-2,3-dihydro-spiro[4H-1-benzopyran-4,4'-imidazolidine]-2',5'-dione;

(−)-1'-{3-[4-(4-fluorophenyl)piperidin-1-yl]propyl}-7-fluoro-2,3-dihydro-spiro[4H-1-benzopyran-4,4'-imidazolidine]-2',5'-dione;

(+/−)-1'-{3-[4-(4-fluoro-2-cyanophenyl)piperidin-1-yl]propyl}-7-chloro-2,3-dihydro-spiro[4H-1-benzopyran-4,4'-imidazolidine]-2',5'-dione;

(+/−)-1'-{3-[4-(4-fluoro-2-cyano-phenyl)piperidin-1-yl]propyl}-7-fluoro-2,3-dihydro-spiro[4H-1-benzothiopyran-4,4'-imidazolidine]-2',5'-dione;

(+/−)-1'-{3-[4-(4-fluoro-2-cyano-phenyl)pipenidin-1-yl]propyl}-7-fluoro-2,3-dihydro-1,1-dioxo-spiro[4H-1-benzothio-pyran-4,4'-imidazolidine]-2',5'-dione;

(+/−)-1'-[3-(4-cyano-4-phenylpiperidin-1-yl)propyl]-6-fluoro-2,3-dihydro-spiro[4H-1-benzopyran-4,4'-imidazolidine]-2',5'-dione;

(+/−)-1'-[3-(4-cyano-4-phenylpiperidin-1-yl)propyl]-3-fluoro-6,7,8,9-tetrahydro-spiro[5H-benzocycloheptene-5,4'-imidazolidine]-2',5'-dione;

(+/−)-1'-{3-[4-(4-fluoro-2-cyano-phenyl)piperidin-1-yl]propyl}-6-fluoro-2,3-dihydro-spiro[1-benzofuran-3(2H),4'-imidazolidine]-2',5'-dione;

(+/−)-1'-{3-[4-(4-fluoro-2-cyano-phenyl)piperidin-1-yl]propyl}-8-fluoro-2,3,4,5-tetrahydro-spiro[1-benzoxepin-5(2H),4'-imidazolidine]-2',5'-dione;

and pharmaceutically acceptable salts thereof.

A preferred aspect of the present invention is a compound selected from the group consisting of (+)-1-{3-[4-(2-cyano-4-fluorophenyl)piperidin-1-yl]propyl}-5'-fluoro-spiro[imidazolidine4,1'indan]-2,5-dione;

(+)-1'-{3-[4-(4-fluoro-2-cyanophenyl)piperidin-1-yl]propyl 3-7-fluoro-2,3-dihydro-spiro[4H-1-benzopyran-4,4'-imidazolidine]-2',5'-dione;

and pharmaceutically acceptable salts thereof.

A third embodiment of the present invention is a compound of Formula (I), wherein Q is

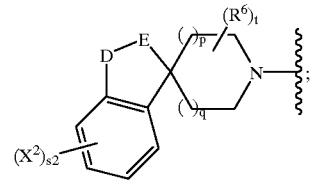

and all other variables are as defined in the first embodiment; or a pharmaceutically acceptable salt thereof.

A second class of the present invention is a compound of Formula (IV):

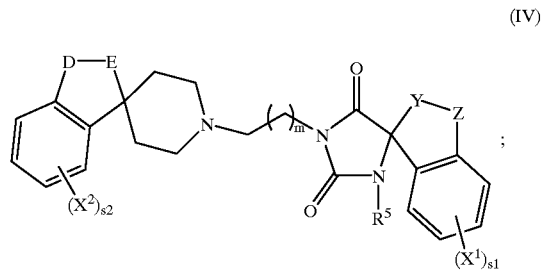

(IV)

wherein $R^5$ is hydrogen, methyl, or ethyl;

Y is $C(R^a)=C(R^b)$, $[C(R^aR^b)]_{1-3}$, or

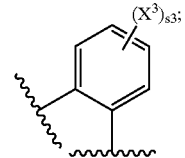

Z is absent, $C(R^aR^b)$, O, S, SO, $SO_2$, or $N(R^c)$; provided that (i) when Z is absent, Y is $C(R^a)=C(R^b)$ or

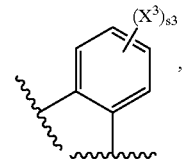

and (ii) when Z is $C(R^aR^b)$, O, S, SO, $SO_2$, or $N(R^c)$, Y is $[C(R^aR^b)]_{1-3}$;

each $X^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^2$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^d$ is hydrogen, methyl, ethyl, or $CF_3$;

m is an integer equal to 2 or 3;

and all other variables are as defined in the third embodiment;

or a pharmaceutically acceptable salt thereof.

A subclass of the preceding class is a compound of Formula (V):

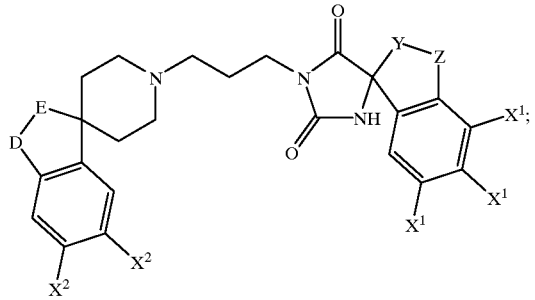

wherein
Y is CH=CH, $(CH_2)_{1-3}$, or

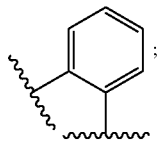

Z is absent, $CH_2$, O, S, SO, or $SO_2$; provided that (i) when Z is absent, Y is CH=CH or

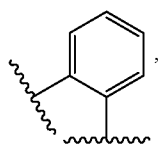

and (ii) when Z is $CH_2$, O, S, SO, or $SO_2$, Y is $(CH_2)_{1-3}$;

D is absent, $[C(R^aR^b)]_{1-4}$, $O[C(R^aR^b)]_{1-2}$, $[C(R^aR^b)]_{1-2}O$, $C(R^a)=C(R^b)$, $C(R^aR^b)-C(R^a)=C(R^b)$, or $C(R^a)=C(R^b)-C(R^aR^b)$;

E is absent, C(=O), C(=O)O, $N(SO_2R^c)C(R^aR^b)$, $N(R^c)C(=O)$, or $N(R^c)C(=O)O$, provided that (i) when E is absent, D is $[C(R^aR^b)]_{2-4}$, $O[C(R^aR^b)]_{1-2}$, $[C(R^aR^b)]_{1-2}O$, $C(R^a)=C(R^b)$, $C(R^aR^b)-C(R^a)=C(R^b)$, or $C(R^a)=C(R^b)-C(R^aR^b)$; (ii) when E is C(=O) or C(=O)O, D is $C(R^aR^b)$ or $C(R^aR^b)C(R^aR^b)$; and (iii) when E is $N(SO_2R^c)C(R^aR^b)$, $N(R^c)C(=O)$ or $N(R^c)C(=O)O$, D is absent or $C(R^aR^b)$;

each $X^1$ is independently hydrogen, fluorine, chlorine, cyano, methyl, ethyl, methoxy, ethoxy, $CF_3$, or $OCF_3$; and each $X^2$ is independently hydrogen, fluorine, chlorine, cyano, methyl, ethyl, methoxy, ethoxy, $CF_3$, or $OCF_3$;

or a pharmaceutically acceptable salt thereof.

Exemplary of compounds of the third embodiment are compounds selected from the group consisting of (+/−)-1-{3-{spiro[indano-1,4'-piperidin]-1-yl}propyl}-5'-fluoro-spiro[imidazolidine-4,1'indan]-2,5-dione;

(+)-1-{3-{spiro[indano-1,4'-piperidin]-1-yl}propyl}-5'-fluoro-spiro[imidazolidine-4,1'indan]-2,5-dione;

(−)-1-{3-{spiro[indano-1,4'-piperidin]-1-yl}propyl}-5'-fluoro-spiro[imidazolidine-4,1'indan]-2,5-dione;

(+/−)-1-{3-{6-chlorospiro[4H-3,1-benzoxazine-4,4'-piperidin]-2(1H)-on-1'-yl}propyl}-5'-fluoro-spiro[imidazol-idine-4,1'indan]-2,5-dione;

(+/−)-1-{3-{spiro[indano-1,4'-piperidine]-1-yl}propyl}-6'-fluoro-spiro[imidazolidine-4,1'indan]-2,5-dione;

(+/−)-1-{3-{spiro[indano-1,4'-piperidin]-1-yl}propyl}-5',6'-difluoro-spiro[imidazolidine-4,1'indan]-2,5-dione;

(+/−)-1-{3-{spiro[indano-1,4'-piperidin]-1-yl}propyl}-5'-chloro-spiro[imidazolide-4,1'indan]-2,5-dione;

(+)-1-{3-{spiro[indano-1,4'-piperidin]-1-yl}propyl}-5'-chloro-spiro[imidazolidine-4,1'indan]-2,5-dione;

(−)-1-{3-{spiro[indano-1,4'-piperidin]-1-yl}propyl}-5'-chloro-spiro[imidazolidine-4,1'indan]-2,5-dione;

(+/−)-1-{3-{6-chlorospiro[4H-3,1-benzoxazine-4,4'-piperidin]-2(1H)-on-1'-yl}propyl}-5'-chloro-spiro[imidazolidine-4,1'indan]-2,5-dione;

(+/−)-1-{3{-spiro[indano-1,4'-piperidin]-1-yl}propyl}-6'-chloro-spiro[imidazoline-4,1'indan]-2,5-dione;

(+/−)-1-{3-{spiro[indano-1,4'-piperidin]-1-yl}propyl}-4'-methyl-spiro[imidazolidine-4,1'indan]-2,5-dione;

(+/−)-1-{3-{spiro[indano-1,4'-piperidin]-1-yl}propyl}-5'-methyl-spiro[imidazolidine-4,1'indan]-2,5-dione;

(+)-1-{3-{spiro[indano-1,4'-piperidin]-1-yl}propyl}-5'-methyl-spiro[imidazolidine-4,1'indan]-2,5-dione;

(−)-1-{3-{spiro[indano-1,4'-piperidin]-1-yl}propyl}-5'-methyl-spiro[imidazolidine-4,1'indan]-2,5-dione;

(+/−)-1-{3-{spiro[indano-1,4'-piperidin]-1-yl}propyl}-6'-methyl-spiro[imidazolidine-4,1'indan]-2,5-dione;

and pharmaceutically acceptable salts thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1and a type 2 (i.e., a three component combination comprising any of the compounds described above combined with both a type 1 testosterone 5-alpha reductase inhibitor and a type 2 testosterone 5-alpha reductase inhibitor), or a dual type 1and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administed in combination with a testosterone 5-alpha reductase inhibitor. A suitable testosterone 5-alpha reductase inhibitor for use in the method is finasteride.

The present invention also includes a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a therapeutically effective amount of a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see Vatz, *Headache* (1997), 37: 107–108) and cardiac arrhythmia.

The present invention also includes a method of preventing or treating prostatic cancer which comprises administering to a subject in need of prevention or treatment thereof a therapeutically effective amount of a combination comprising any of the compounds (or compositions) described above and a testosterone 5-alpha reductase inhibitor. The testosterone 5-alpha reductase inhibitor is suitably finasteride.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy.

The term "$C_2$–$C_8$ alkoxyalkyl" means a linear or branched $C_1$–$C_6$ alkyl group as defined above having as a substituent a $C_1$–$C_6$ alkoxy group as defined above, wherein the alkoxyalkyl group has a total of from 2 to 8 carbon atoms. Representative examples of suitable alkoxyalkyl groups include, but are not limited to, the $C_1$–$C_6$ alkoxy-substituted methyl groups (methoxymethyl, ethoxymethyl, n-propoxymethyl, isopropoxymethyl, and the butyloxymethyl, pentyloxymethyl, and hexyloxymethyl isomers), and the $C_1$–$C_6$ alkoxy-substituted ethyl groups. Other suitable alkoxyalkyl groups include the series $(CH_2)_{1-6}OCH_3$, $(CH_2)_{1-4}OCH_3$, $(CH_2)_{1-6}OCH_2CH_3$, and $(CH_2)_{1-4}OCH_2CH_3$.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). The term "$C_3$–$C_6$ cycloalkyl" refers to a cyclic ring selected from cyclopropyl, cyclobutyl, cyclopentyl, and cyclohexyl. "$C_4$–$C_6$ cycloalkyl" has an analogous meaning.

The term "halogen" (which may alternatively be referred to as "halo") refers to fluorine, chlorine, bromine and iodine (alternatively, fluoro, chloro, bromo, and iodo).

The term "fluorinated $C_1$–$C_6$ alkyl" (which may alternatively be referred to as "$C_1$–$C_6$ fluoroalkyl") means a $C_1$ to $C_6$ linear or branched alkyl group as defined above with one or more fluorine substituents. The term "fluorinated $C_1$–$C_4$ alkyl" has an analogous meaning. Representative examples of suitable fluoroalkyls include the series $(CH_2)_{0-4}CF_3$ (i.e., tnrfluoromethyl, 2,2,2-trifluoroethyl, 3,3,3-trifluoron-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_3$–$C_8$ cycloalkyl" (which may alternatively be referred to as "$C_3$–$C_8$ fluorocycloalkyl") means a cycloalkyl group as defined above with one or more fluorine substituents. The terms "fluorinated $C_3$–$C_7$ cycloalkyl" and "fluorinated $C_3$–$C_6$ cycloalkyl" have analogous meanings. Representative examples of suitable fluorocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), fluorocyclopentyl, and so forth.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The term "fluorinated $C_1$–$C_4$ alkoxy" has an analogous meaning. Representative examples include the series $O(CH_2)_{0-4}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "fluorinated $C_2$–$C_8$ alkoxyalkyl" means $C_2$–$C_8$ alkoxyalkyl as defined above, wherein either or both the alkoxy moiety and the alkyl moiety has one or more fluorine substituents. Representative examples of suitable fluorinated alkoxyalkyl groups include, but are not limited to, the $C_1$–$C_6$ fluoroalkoxy-substituted methyl groups (e.g., fluoromethoxymethyl, 2-fluoroethoxymethyl, and 3-fluoro-n-propoxymethyl), $C_1$–$C_6$ difluoroalkoxymethyl groups (e.g., difluoromethoxymethyl and 2,2-difluoroethoxymethyl), $C_1$–$C_6$ trifluoroalkoxy-substituted methyl groups (e.g., trifluoromethoxymethyl and 2,2,2-trifluoroethoxymethyl), $C_1$–$C_6$ alkoxy-substituted fluoromethyl groups (e.g., methoxy or ethoxy-fluoromethyl and $C_1$–$C_6$ alkoxy-substituted difluoromethyl groups (e.g., methoxy- or ethoxy-difluoromethyl). Other suitable fluorinated alkoxyalkyl groups include the series $(CH_2)_{1-6}OCF_3$, $(CH_2)_{1-4}OCF_3$, $(CH_2)_{1-6}OCH_2CF_3$, and $(CH_2)_{1-4}OCH_2CF_3$.

The term "heterocyclic" (which may alternatively be referred to as "heterocycle") refers to a stable 5- to 7-membered monocyclic ring system which may be saturated or unsaturated; which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any single heteroatom or carbon atom, provided that attachment results in the creation of a stable structure. Suitable heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxadiazolyl, triazolyl, oxazolidinyl, isooxazolyl, isoxazolidinyl, morpholinyl, thiazolyl, thiazolidinyl, isothiazolyl, thiadiazolyl, tetrahydropyranyl, thiomorpholinyl, thiomorpholinyl sulfoxide, thiamorpholinyl sulfone, and oxadiazolyl. Morpholino is the same as morpholinyl.

The term "thienyl," as used herein, refers to the group

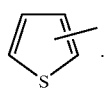

The term "substituted heterocyclic" refers to a heterocyclic group as defined above having one or more substituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N—($C_1$–$C_6$ alkyl)amino, N,N-di-($C_1$–$C_6$ alkyl)amino, N,N-di-($C_1$–$C_6$ alkyl)amino, aryl (defined below), carboxy, $C_1$–$C_6$ alkoxycarbonyl, sulfonamido, sulfonyl, and the like.

The term "aryl" refers herein to aromatic mono- and poly-carbocyclic ring systems, wherein the carbocyclic rings in the polyring systems may be fused or attached via a single ring carbon. Suitable aryl groups include, but are not limited to, phenyl, naphthyl, and biphenylenyl.

"Substituted aryl" refers to aryl groups as defined above having one or more substituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N—$C_1$–$C_6$ alkylamino, N,N-di-($C_1$–$C_6$)alkylamino, aryl, carboxy, $C_1$–$C_6$ alkoxycarbonyl, sulfonamido, sulfonyl, and the like.

The term "heteroaryl" refers to the subset of heterocycles as heretofore defined which are aromatic heterocyclic ring systems, including, but not limited to, pyridyl, pyrazinyl, thienyl, thiazolyl, furanyl, imidazolyl, pyrazolyl, triazolyl, oxazolyl, oxadiazolyl, thiazolyl, and thiadiazolyl.

"Substituted heteroaryl" refers to heteroaryl groups as defined above having one or more substituents as defined above.

The term "substituted" includes mono- and poly-substitution by a named substituent to the extent such single and multiple substitution is chemically allowed.

The expression "Z is absent" means that Z is replaced by a bond connecting the atoms/moieties to which Z would otherwise be attached; i.e., when Z is absent, the compound of Formula (I) may be represented as:

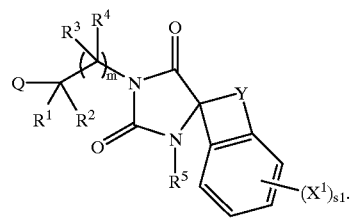

It is understood that the definition of a substituent (e.g., $CO_2R^d$) or variable (e.g., $R^d$) at a particular location in a molecule is independent of its definitions at other locations in that molecule. Thus, for example, when $R^7$ is $CO_2R^d$=$CO_2H$, and $R^8$ is substituted phenyl wherein at least one of the substituents is $CO_2R^d$, it is understood that $CO_2R^d$ on $R^8$ can be any one of $CO_2H$, $CO_2Me$, $CO_2Et$, $CO_2Pr$, etc. As another example, the definitions of $R^a$ and $R^b$ in D, E, Y, and Z are independent of each other. As still another example, the moiety

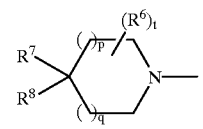

wherein $R^6$ is hydrogen or $C_1$–$C_4$ alkyl, p=1, q=1, and t=2, represents moieties such as

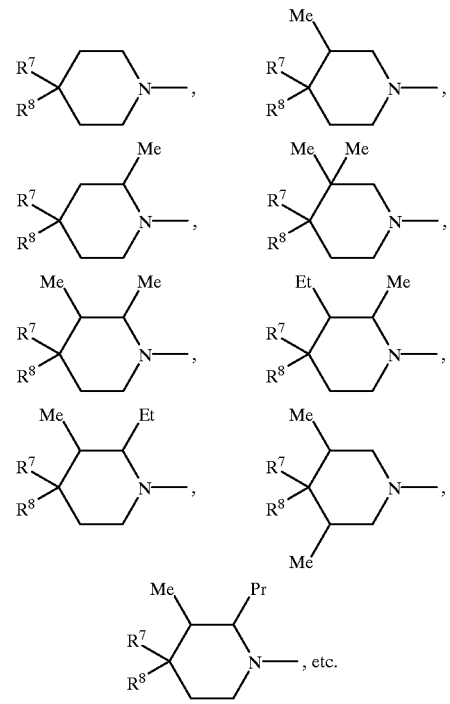

It is also understood that the definition of a substituent or variable at a particular location in a molecule is independent of the definition of another occurrence of the same substituent or variable at the same location. Thus, $C(=O)N(R^d)_2$ represents groups such as —C(=O)NH2, —C(=O)NHCH_3, —C(=O)NHC_2H_5, —C(=O)N(CH_3)C_2H_5, etc.

It is understood that substituents and substitution patterns on the compounds of the instant invention can be selected by one of ordinary skill in the art to provide compounds that are chemically stable and that can be readily synthesized by the methods set forth below and, when viewed in the light of this disclosure, by techniques known in the art. Where multiple substituent moieties are disclosed or claimed, the substituted compound can be independently substituted by one or more of the disclosed or claimed substituent moieties, singly or plurally.

Representative embodiments for the variables and substituents set forth in Formula (I) include the following:

One of $R^1$ and $R^2$ is hydrogen or fluorine and the other of $R^1$ and $R^2$ is hydrogen, fluorine, $C_1$–$C_6$ alkyl, or $C_3$–$C_8$ cycloalkyl. In other embodiments, each of $R^1$ and $R^2$ is hydrogen, fluorine, or $C_1$–$C_4$ alkyl; or is hydrogen, fluorine, methyl, or ethyl; or is hydrogen or fluorine; or is hydrogen; or is fluorine.

One of $R^3$ and $R^4$ is hydrogen or fluorine and the other of $R^3$ and $R^4$ is hydrogen, fluorine, $C_1$–$C_6$ alkyl, or $C_3$–$C_8$ cycloalkyl. In other embodiments, each of $R^3$ and $R^4$ is hydrogen, fluorine, or $C_1$–$C_4$ alkyl; or is hydrogen, fluorine, methyl, or ethyl; or is hydrogen or fluorine; or is hydrogen; or is fluorine.

In another embodiment, one of $R^1$ and $R^2$ is hydrogen and the other is fluorine, and one of $R^3$ and $R^4$ is hydrogen and the other is fluorine (i.e., the chain linking Q to the spirohydantoin moiety is $(CHF)_{m+1}$.)

$R^5$ is hydrogen, $C_1$–$C_4$ alkyl, fluorinated $C_1$–$C_4$ alkyl, $C_3$–$C_6$ cycloalkyl, fluorinated $C_3$–$C_6$ cycloalkyl, $(CH_2)_{1-2}CO_2R^d$, $(CH_2)_{1-2}C(=O)N(R^d)_2$, $C_2$–$C_8$ alkoxyalkyl, or fluorinated $C_2$–$C_8$ alkoxyalkyl; or is hydrogen, $C_1$–$C_4$ alkyl, $(CH_2)_{1-3}CF_3$, $C_3$–$C_6$ cycloalkyl, fluorinated $C_3$–$C_6$ cycloalkyl, $(CH_2)_{1-2}CO_2R^d$, $(CH_2)_{1-2}C(=O)N(R^d)_2$, $(CH_2)_{1-3}OCH_3$, or $(CH_2)_{1-3}OCF_3$: or is hydrogen, $C_1$–$C_4$ alkyl, or $(CH_2)_{1-3}CF_3$; or is hydrogen, methyl, or ethyl; or is hydrogen.

Each $R^6$ is a substituent connected to a ring atom other than $C(R^7R^8)$, spiro substituted carbon, or N and is independently hydrogen, methyl, or ethyl; or is hydrogen.

$R^7$ is hydrogen, cyano, hydroxy, $CO_2R^d$, $CON(R^d)_2$, substituted aryl; or is cyano, $CO_2R^d$, $CON(R^d)_2$, or substituted aryl; or is hydrogen, cyano, hydroxy, $CO_2R^d$, CON $(R^d)_2$, phenyl, or substituted phenyl; or is hydrogen, cyano, hydroxy, $CO_2R^d$, $CON(R^d)_2$, phenyl, or mono- or di- or tri-substituted phenyl; or is hydrogen, cyano, hydroxy, $CO_2R^d$, $CON(R^d)_2$, phenyl, or mono- or di-substituted phenyl; or is cyano, $CO_2R^d$, $CON(R^d)_2$, or mono- or di-substituted phenyl; or is hydrogen or cyano; or is cyano.

It is understood that the definition of $R^7$ in the preceding embodiments is subject to and to be read together with the proviso, set forth elsewhere, concerned with compounds having Q of formula (a1). This proviso is controlling, and thus can restrict or exclude one or more of the embodiments of $R^7$, with respect to compounds having Q=a1.

When $R^7$ is substituted aryl (e.g., substituted phenyl), each of the substituents on substituted aryl is independently halo, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, $(CH_2)_{0-4}CO_2R^d$, $C_2$–$C_8$ alkoxyalkyl, or fluorinated $C_2$–$C_8$ alkoxyalkyl; or each is independently fluorine, chlorine, cyano, hydroxy, methyl, ethyl, $CF_3$, $OCH_3$, $(CH_2)_{1-2}OCH_3$, $(CH_2)_{1-2}OCF_3$, $CO_2CH_3$, or $CH_2CO_2CH_3$.

$R^8$ is phenyl, substituted phenyl, naphthyl, or substituted naphthyl; or pyridyl, pyrazinyl, thienyl, or furanyl; or substituted pyridyl, pyrazinyl, thienyl, or furanyl. In another embodiment, $R^8$ is phenyl, naphthyl, pyridyl, pyrazinyl, thienyl, or furanyl; or mono- or di- or tri-substituted phenyl, naphthyl, pyridyl, pyrazinyl, thienyl, or furanyl. In still other embodiments, $R^8$ is phenyl, mono- or di- or tri-substituted phenyl, pyridyl, pyrazinyl, substituted pyridyl, or substituted pyrazinyl; or is phenyl, substituted phenyl, or pyridyl.

When $R^8$ is substituted aryl (e.g., substituted phenyl or substituted naphthyl), each of the substituents is independently halo, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, $(CH_2)_{0-4}CO_2R^d$, $(CH_2)_{0-4}C(=O)N(R^d)_2$, $C_2$–$C_8$ alkoxyalkyl, or fluorinated $C_2$–$C_8$ alkoxyalkyl; or is independently chlorine, fluorine, $C_1$–$C_4$ alkyl, $(CH_2)_{0-3}CF_3$, $C_1$–$C_4$ alkoxy, $OCF_3$, $(CH_2)_{0-4}CO_2CH_3$, $(CH_2)_{1-3}OCH_3$, or $(CH_2)_{1-3}OCF_3$; or is independently halogen or cyano.

When $R^8$ is substituted heteroaryl (e.g., substituted pyridyl, pyrazinyl, thienyl, or furanyl), each of the substituents is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl, $C_1$–$C_4$ alkyl, fluorinated $C_1$–$C_4$ alkyl, $C_1$–$C_4$ alkoxy, fluorinated $C_1$–$C_4$ alkoxy, $(CH_2)_{0-4}CO_2R^d$, $C_2$–$C_8$ alkoxyalkyl, or fluorinated $C_2$–$C_8$ alkoxyalkyl; or is chlorine, fluorine, $C_1$–$C_4$ alkyl, $(CH_2)_{0-3}CF_3$, $C_1$–$C_4$ alkoxy, $OCF_3$, $(CH_2)_{0-4}CO_2CH_3$, $(CH_2)_{1-3}OCH_3$, or $(CH_2)_{1-3}OCF_3$; or is independently halogen or cyano.

$R^{10}$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl; or is hydrogen, methyl, ethyl, $CF_3$, $CH_2CF_3$, or $C_3$–$C_6$ cycloalkyl; or is hydrogen.

$R^{12}$ is hydrogen, methyl or ethyl; or is hydrogen.

Each $X^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCF_3$, or $(CH_2)_{1-4}OCF_3$; or is independently hydrogen, chlorine, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$; or is independently hydrogen, fluorine, chlorine, cyano, methyl, ethyl, methoxy, ethoxy, $CF_3$, or $OCF_3$; or is independently hydrogen, fluorine, chlorine, or methyl; or is independently hydrogen or fluorine.

Y is $[C(R^aR^b)]_{1-3}$ or

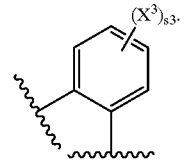

In another embodiment, Y is $(CH_2)_{1-3}$.

Z is absent, $C(R^aR^b)$, O, S, SO, or $SO_2$; provided that (i) when Z is absent, Y is

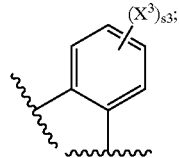

and (ii) when Z is $C(R^aR^b)$, O, S, SO, or $SO_2$, Y is $[C(R^aR^b)]_{1-3}$. In another embodiment, Z is absent, $CH_2$, O, S, SO, or $SO_2$, with the same provisos as in the preceding sentence.

The spirohydantoin moiety of the compounds of the invention include the following, which represent particular combinations of Y and Z:

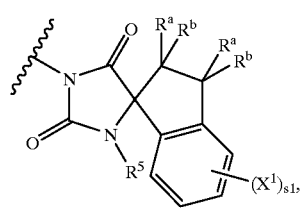

Y = Z = $CR^aR^b$

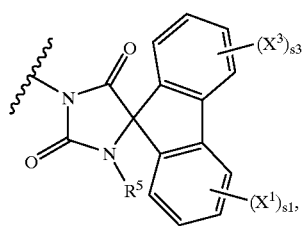

Z is absent

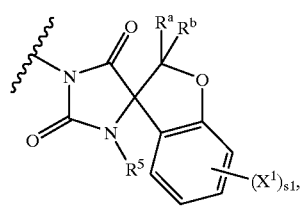

Z = O; Y = $CR^aR^b$

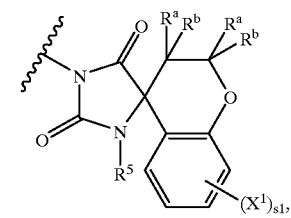

Z = O; Y = $[C(R^aR^b)]_2$

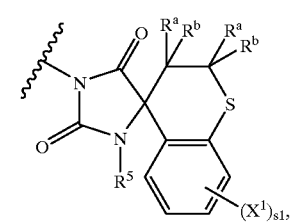

Z = S; Y = $[C(R^aR^b)]_2$

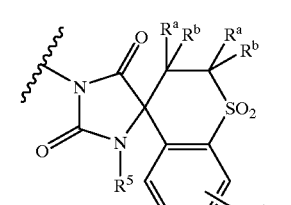

Z = $SO_2$; Y = $[C(R^aR^b)]_2$

-continued

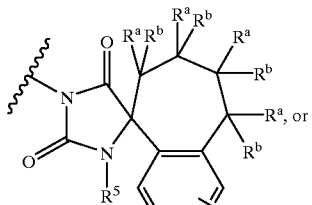

Z = $C(R^aR^b)$; Y = $[C(R^aR^b)]_3$

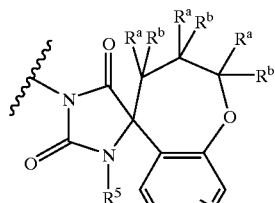

Z = O; Y = $[C(R^aR^b)]_3$

D is absent, $[C(R^aR^b)]_{1-4}$, or $O[C(R^aR^b)]_{1-2}$; or D is absent or $(CH_2)_{1-4}$.

E is absent, C(=O), C(=O)O, $N(R^c)C(=O)$, or $N(R^c)C(=O)O$, provided that (i) when E is absent, D is $[C(R^aR^b)]_{2-4}$ or $O[C(R^aR^b)]_{1-2}$; (ii) when E is C(=O) or C(=O)O, D is $C(R^aR^b)$ or $C(R^aR^b)C(R^aR^b)$; and (iii) when E is $N(R^c)C(=O)$ or $N(R^c)C(=O)O$, D is absent or $C(R^aR^b)$.

Groups of formula (a2) include the following, which represent particular combinations of D and E:

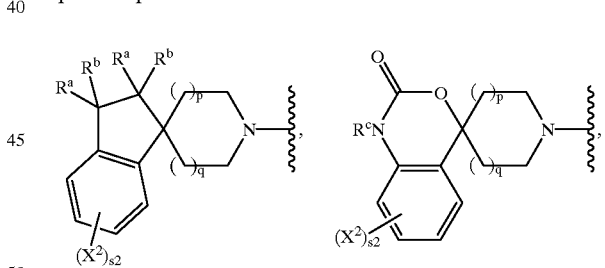

D is $[C(R^aR^b)]_2$;      D is absent;
E is absent              E is $N(R^c)C(=O)O$

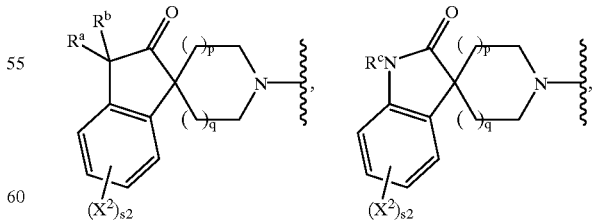

D is $C(R^aR^b)$;         D is absent
E is C(=O)               E is $N(R^c)C(=O)$

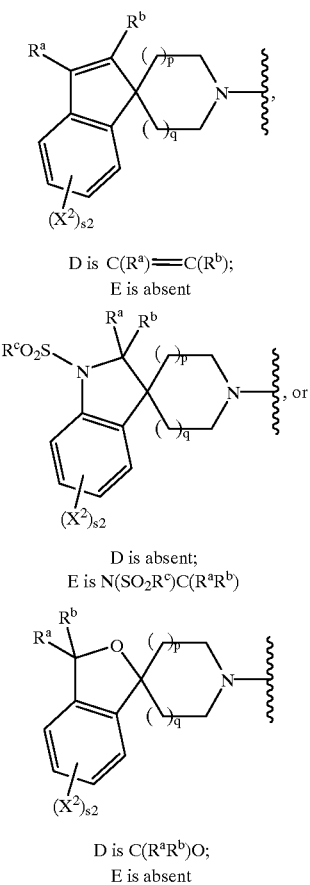

D is C(R$^a$)=C(R$^b$);
E is absent

D is absent;
E is N(SO$_2$R$^c$)C(R$^a$R$^b$)

D is C(R$^a$R$^b$)O;
E is absent

Each X$^2$ is independently hydrogen, halogen, cyano, C$_1$–C$_4$ alkyl, (CH$_2$)$_{0-4}$CF$_3$, C$_1$–C$_4$ alkoxy, OCF$_3$, (CH$_2$)$_{0-4}$CO$_2$R$^d$, (CH$_2$)$_{1-4}$OCH$_3$, or (CH$_2$)$_{1-4}$OCF$_3$; or is independently hydrogen, chlorine, fluorine, cyano, methyl, ethyl, CF$_3$, methoxy, ethoxy, OCF$_3$, CO$_2$CH$_3$, CH$_2$CO$_2$CH$_3$, (CH$_2$)$_{1-4}$OCH$_3$, or (CH$_2$)$_{1-4}$OCF$_3$; or is independently hydrogen, fluorine, chlorine, cyano, methyl, ethyl, methoxy, ethoxy, CF$_3$, or OCF$_3$; or is independently hydrogen, fluorine, chlorine, or methyl; or is independently hydrogen or fluorine.

Each X$^3$ is independently hydrogen, halogen, cyano, C$_1$–C$_4$ alkyl, (CH$_2$)$_{0-4}$CF$_3$, C$_1$–C$_4$ alkoxy, OCF$_3$, (CH$_2$)$_{0-4}$CO$_2$R$^d$, (CH$_2$)$_{1-4}$OCH$_3$, or (CH$_2$)$_{1-4}$OCF$_3$; or is independently hydrogen, chlorine, fluorine, cyano, methyl, ethyl, CF$_3$, methoxy, ethoxy, OCF$_3$, CO$_2$CH$_3$, CH$_2$CO$_2$CH$_3$, (CH$_2$)$_{1-4}$OCH$_3$, or (CH$_2$)$_{1-4}$OCF$_3$; or is independently hydrogen, fluorine, chlorine, cyano, methyl, ethyl, methoxy, ethoxy, CF$_3$, or OCF$_3$; or is independently hydrogen, fluorine, chlorine, or methyl; or is independently hydrogen or fluorine.

A particular embodiment of Q is (a1) of formula:

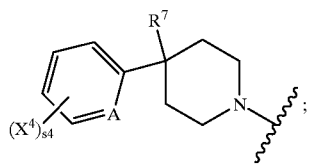

wherein A is N or CX$^4$; R$^7$ is defined elsewhere; X$^4$ has the same definition as X$^3$; and s4 is an integer from 0 to 3, or from 0 to 2.

R$^a$ and R$^b$ are each independently selected from hydrogen, C$_1$–C$_4$ alkyl, and (CH$_2$)$_{0-4}$CF$_3$; or are each independently selected from hydrogen, methyl, and ethyl; or are each independently selected from hydrogen and methyl; or are both hydrogen.

R$^c$ is hydrogen, C$_1$–C$_4$ alkyl, or (CH$_2$)$_{0-4}$CF$_3$; or is hydrogen, methyl, or ethyl; or is hydrogen.

R$^d$ is hydrogen, C$_1$–C$_4$ alkyl, or (CH$_2$)$_{0-4}$CF$_3$; or is hydrogen, methyl, ethyl, or CF$_3$; or is hydrogen.

m is an integer from 1 to 3; or is 2 or 3; or is 2.

p and q are each integers from 0 to 3, provided that the sum of p+q is an integer less than or equal to 3. In another embodiment p and q are each independently integers from 0 to 1. In still another embodiment p and q are both 1.

s1 is an integer from 0 to 3; or from 0 to 2; or is 0 or 1.
s2 is an integer from 0 to 3; or from 0 to 2; or is 0 or 1.
s3 is an integer from 0 to 3; or from 0 to 2; or is 0 or 1.
t is an integer from 0 to 2; or is 0 or 1; or is zero.

The compounds of the present invention typically exhibit selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying lower affinity for the human alpha 1d and alpha 1b adrenergic receptor subtypes, and many other G-protein coupled human receptors. A class of the compounds of this invention exhibit nanomolar and subnanomolar affinity for the human alpha 1a adrenergic receptor subtype while displaying at least about 10 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). In a subclass of the preceding class, the compounds of this invention exhibit nanomolar and subnanomolar affinity for the human alpha 1a adrenergic receptor subtype while displaying at least about 40-fold lower affinity for the human alpha 1d and alpha 1b adrenergic receptor subtypes, in addition to exhibiting selectivity over other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intraocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

The compounds according to the invention have at least one chiral center, and they may accordingly exist as enantiomers or as mixtures of enantiomers (e.g., racemic mixtures). Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which exhibits selectivity (e.g., at least about ten fold selectivity) for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued April 4, 1995]. Compounds which are both selective amongst the various human alpha1 adrenergic receptor subtypes and which have low affinity for other receptors, such as the alpha 2 adrenergic receptors, the β-adrenergic receptors, the muscarinic receptors, the serotonin receptors, the histamine receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin. Other dispersing agents which may be employed include glycerin and the like.

For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO 93/23420, EP 0572166; WO 93/23050; WO 93/23038; WO 93/23048; WO 93/23041; WO 93/23040; WO 93/23039; WO 93/23376; WO 93/23419, EP 0572165; WO 93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. No. 4,377,584 and U.S. Pat. No. 4,760,071 which describe dosages and formulations for 5a-reductase inhibitors.

Abbreviations used in the instant specification, particularly the Schemes and Examples, are as follows:

Boc or BOC=t-butyloxycarbonyl
Bu=butyl

DMF=N,N-dimethylformamide
EDTA=ethylenediamine tetraacetic acid
Et=ethyl
$Et_3N$=triethylamine
EtOAc=ethyl acetate
EtOH=ethanol
HPLC=high performance liquid chromatography
Me=methyl
m.p.=melting point
p-MeOBzBr=p-methoxybenzylbromide
Ph=phenyl
Pr=propyl
TFA=trifluoroacetic acid
THF=tetrahydrofuran The compounds of the present invention can be readily prepared according to the following reaction schemes and examples, or modifications thereof, using readily available starting materials, reagents and conventional synthetic procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Many of the compounds claimed within this invention can be prepared via Schemes 1–4 shown below. Scheme 1 describes the preparation of compounds of Formula (I) in which Z is absent or $C(R^aR^b)$, wherein the spiroimidazolidine-2,5-dione precursor can be prepared from the corresponding benzo-substituted cyclic ketone by heating the ketone with cyanide and ammonium carbonate in wet DMF. The spiroimidazolinedione precursor can then be alkylated at the N-1 nitrogen with a suitable dihaloalkane (e.g. 1,3-dibromopropane) to obtain a 1-haloalkyl spiroimidazolidinedione intermediate, which can then be aminated by heating with amine Q—H in dry DMF and triethylamine to provide the compound of the invention.

Scheme 2 describes the preparation of compounds identical to those of Scheme 1, except that the N-3 nitrogen of the spirohydantoin ring has a substituent other than H (i.e., $R^5$ is not hydrogen). This scheme is similar to Scheme 1, except that the N-1 nitrogen on the spirohydantoin ring (the more reactive nitrogen) is first protected with a removable protecting group such as p-methoxybenzyl, then the $R^5$ group is introduced (e.g., alkylating with an alkyl bromide to introduce an alkyl group). The protecting group can then be removed with ceric ammonium nitrate in aqueous acetonitrile and the N-1 nitrogen can be alkylated and then aminated as in Scheme 1. Other approaches which can be utilized involve incorporation of the desired compatible substituted nitrogen during a stepwise construction of the hydantoin ring. These other alternative routes are described generally in Ware, Chem. Rev. 1950, 46: 403–457.

Schemes 3 and 4 describe the preparation of compounds of Formula (I) in which Z is O, S, SO, $SO_2$, or $NR^c$. Schemes 3 and 4 are analogous to Schemes 1 and 2 respectively.

The amines of formula Q—H which are coupled to the spirohydantoin intermediates to obtain compounds of the invention are readily available from commercial sources and/or can be prepared using procedures the same or similar to those known in the art. Thus, for example, amines Q—H with Q of formula al can be prepared as illustrated in Scheme 5 for aryl- and heteroaryl-piperidines. In accordance with Scheme 5-A, 1-Boc-4-piperidone can be reacted with LDA and n-phenyltrifluoromethane sulfonimide to provide the 1,2,5,6-tetrahydropyridin-4-yl ester of trifluoromethane sulfonic acid which, upon reaction with aryl zinc iodide in the presence of tetrakis (triphenylphosphine) palladium will provide 1-Boc-4-aryl-1,2,5,6-tetrahydropyridine which is hydrogenated to 1-Boc-4-arylpiperidine, followed by deprotection (e.g., by reaction with HCl) to obtain the piperidine. Scheme 5-B is a variation of 5-A in which 4-aryl-4-hydroxypiperidin-1-yl substituents can be obtained. In accordance with 5-B, an arylmagnesium bromide can be reacted with 1-Boc-4-piperidone to obtain 1-Boc-4-aryl-4-hydroxy piperidine which can be deprotected (e.g., by reation with HCl). Scheme 5–C provides a general method for preparing 4-aryl-4-cyanopiperidines. Arylacetonitrile accordingly can be reacted with bis-2-chloroethyl-tert-butoxycarbonylamine and NaH or cesium carbonate to provide 1-Boc-4-aryl-4-cyano-piperidine, which can be deprotected by conventional procedures (e.g., by reaction with HCl.)

Further description of the preparation of suitable amines Q—H with Q=a1 can be found in U.S. Pat. No. 5,661,163 and in WO 96/19967.

Many of the amines Q—H with Q of formula a2 can be prepared by the methods set forth in Schemes 6–10 below. Scheme 6 shows the preparation of spiroindanyl- and spiroindenyl-piperidines, wherein indene L1 is reacted with a strong base (e.g., LHMDA, LDA, or sodium or potassium hydride) and then with N-Boc-bis-(2-chloroethyl)amine to form the Boc-protected spiroindene piperidine L2, which is treated with acid (e.g., TFA in $CH_2Cl_2$ or HCl in cold EtOAc) to obtain spiro[1H-indeno-1,4'-piperidine] L3. Reduction of L2 ($H_2$ and palladium on carbon catalyst) followed by nitrogen deprotection (or, alternatively, reduction of L3) affords the spiro[indano-1,4'-piperidine] L4. For further description of this chemistry, see J. Med. Chem. 1992, 35: 2033–2039 and 3919–3927.

Other N-Boc-bis-(haloalkyl)amines can be used in place of N-Boc-bis(2-chloroethyl)amine to provide a wide range of spiroindene and spiroindane azacycloalkanes suitable for preparing compounds of the invention; i.e., Boc-protected amines of formula:

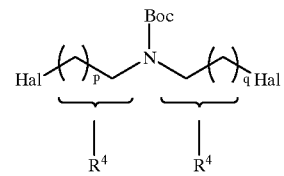

can be used to obtain spirocyclic amines of formula:

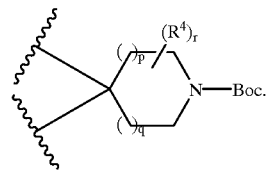

Scheme 7 provides a method for forming spiro[indano-1,4'-piperidin]-2-ones, wherein Boc-protected spiroindene piperidine L5 is treated with a peroxy acid to obtain epoxide intermediate L6, which forms the corresponding spiroindan-2-one L7 upon treatment with a Lewis acid. Nitrogen deprotection by treatment with an acid such as TFA provides L8. Alternatively, L7 can be alkylated on the indanone ring by reaction with alkyl halide and then nitrogen deprotected to afford L9.

Scheme 8 shows a method for forming spiro [isobenzofuran-1(3H),4'-piperidines] and spiro [isobenzofuran-1(3H),4'-piperidin]-3-ones. N-phenylbenzamide L10 is lithiated with n-butyllithium and then reacted with N-Boc-piperidone to afford N-Boc-spiro [isobenzofuran-1(3H),4'-piperidin]-3-one L11, which can be treated with acid to form the deprotected analog L12. Alternatively, L11 can be reduced with borane and then deprotected to provide spiro[isobenzofuran-1(3H),4'-piperidine] L13. Further description of this chemistry can be found in *J. Org. Chem.* 1975, 40: 1427–1433.

Scheme 9 shows a method for forming spiro[3H-indole-3,4'-piperidin]-2(1H)-ones, in which 3H-indol-2(1H)-one L14 is treated with a strong base (e.g., LHMDA, LDA, or sodium or potassium hydride) and then with N-Boc-bis-(2-chloroethyl)amine to form the Boc-protected spiroindolyl piperidine L15, which is treated with acid (e.g., TFA in $CH_2Cl_2$ or HCl in cold EtOAc) to obtain L16. Further description of this chemistry can be found in *Org. Prep. Proced. Int.* 1995, 27: 691–694. [Note: This reference teaches that the first step of Scheme 9 works with a benzyl-protected reagent, but not with a Boc-protected reagent. Boc-protected reagents have been found herein to work satisfactorily with a suitable choice of strong base.] As noted above in discussing Scheme 6, other N-Boc-bis-(haloalkyl) amines can be used in place of N-Boc-bis(2-chloroethyl) amine in this scheme to provide a variety of analogs of L16.

Scheme 10 shows a method for forming spiro[4H-3,1-benzoxazine-4,4'-piperidine]-2(1H)-ones. Halo-substituted aniline L17 is treated with di-t-butylcarbonate to obtain L18, which is lithiated with t-butyllithium and reacted with a Boc'ed piperidone to obtain Boc-protected halobenzoxazinone L19, which can be deprotected by treatment with an acid to form L21, or can be N-alkylated on the benzoxazine ring by treatment with an alkyl halide and then deprotected to form L22. Alternatively, L19 can be dehalogenated by treatment with $H_2/Pd$ to obtain L20, which can then be nitrogen-deprotected to afford L23, or can be N-alkylated and deprotected to form L24. Further description of this chemistry can be found in *J. Med. Chem.* 1983, 26: 657–661, *Chem. Pharm. Bull.* 1985, 33: 1129–1139, and U.S. Pat. No. 4,349,549.

Methods for preparing a variety of 1,2-dihydro-spiro[3H-indole-3,4'-piperidines] are disclosed in U.S. Pat. No. 5,536,716. For example, the preparations of 1,2-dihydro-1-methanesulfonylspiro[3H-indole-3,4'-piperidine] and spiro [3H-indole-3,4'-piperidine] are respectively described in Example 18, Step A and in Example 21, Step A.

Amines Q—H with Q of formula a3 can be prepared in accordance with procedures described in WO 96/25934 corresponding to U.S. Pat. Nos. 5,952,351 and 6,096,763. Amines with Q of formula a4 can be prepared by the reductive amination of cycloalkanones, as described in WO 98/57632, corresponding to U.S. Pat. No. 6,057,350, using ammonia instead of a diamine. Amines with Q of formula a5 can be prepared by the reductive amination of cycloazaalkanones (e.g., piperidones) as described in WO 98/57638, using ammonia instead of a diamine.

SCHEME 1

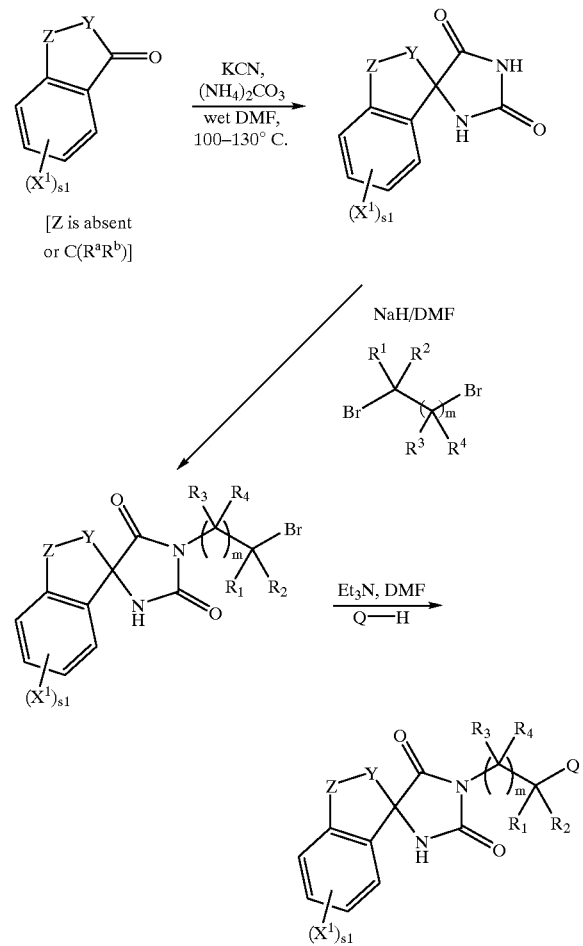

SCHEME 2

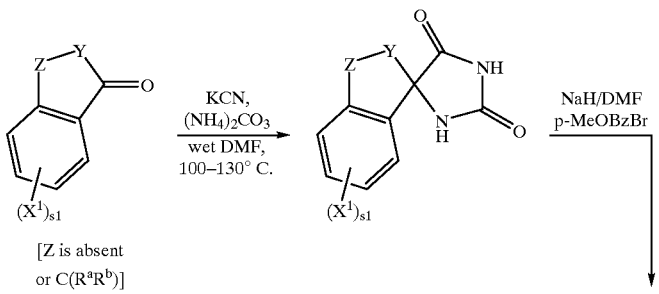

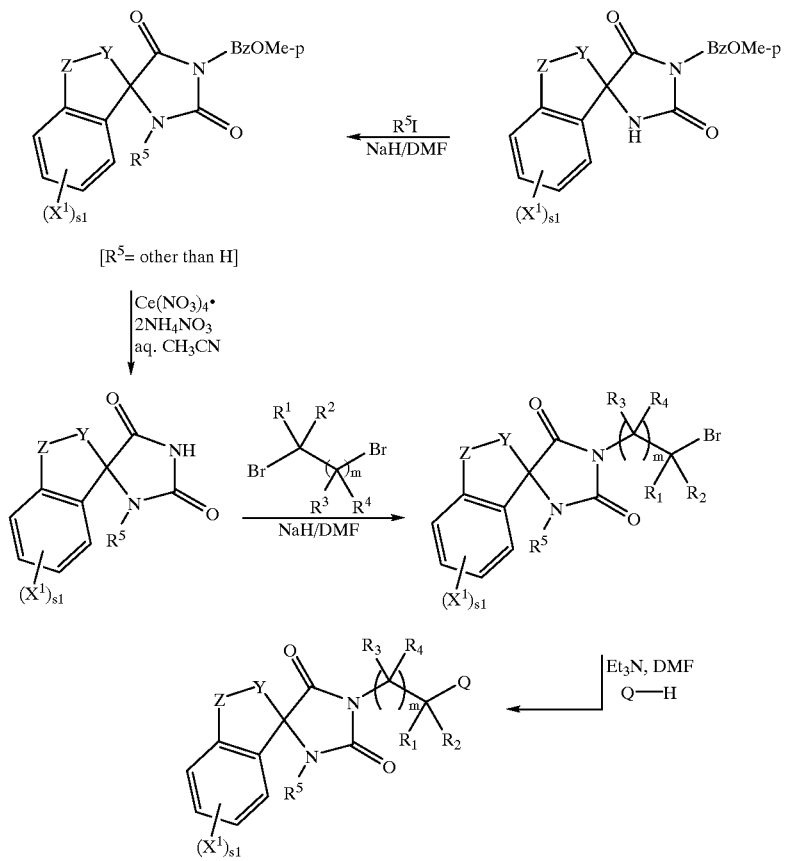
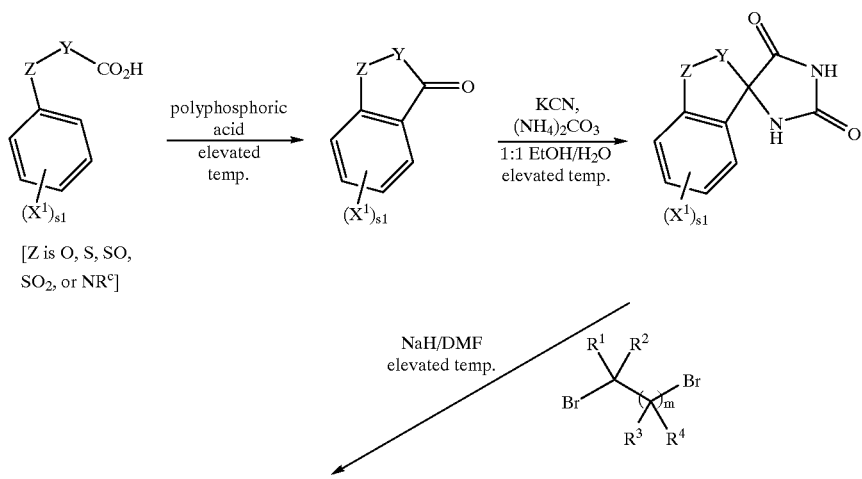
SCHEME 3

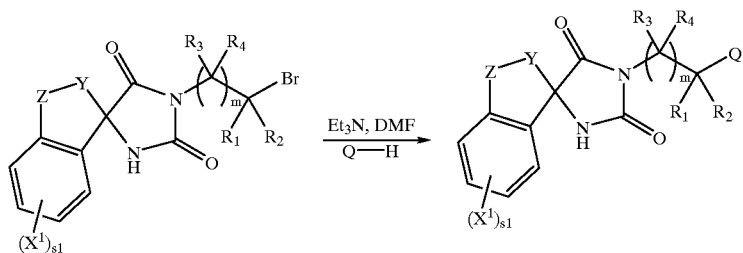
SCHEME 4
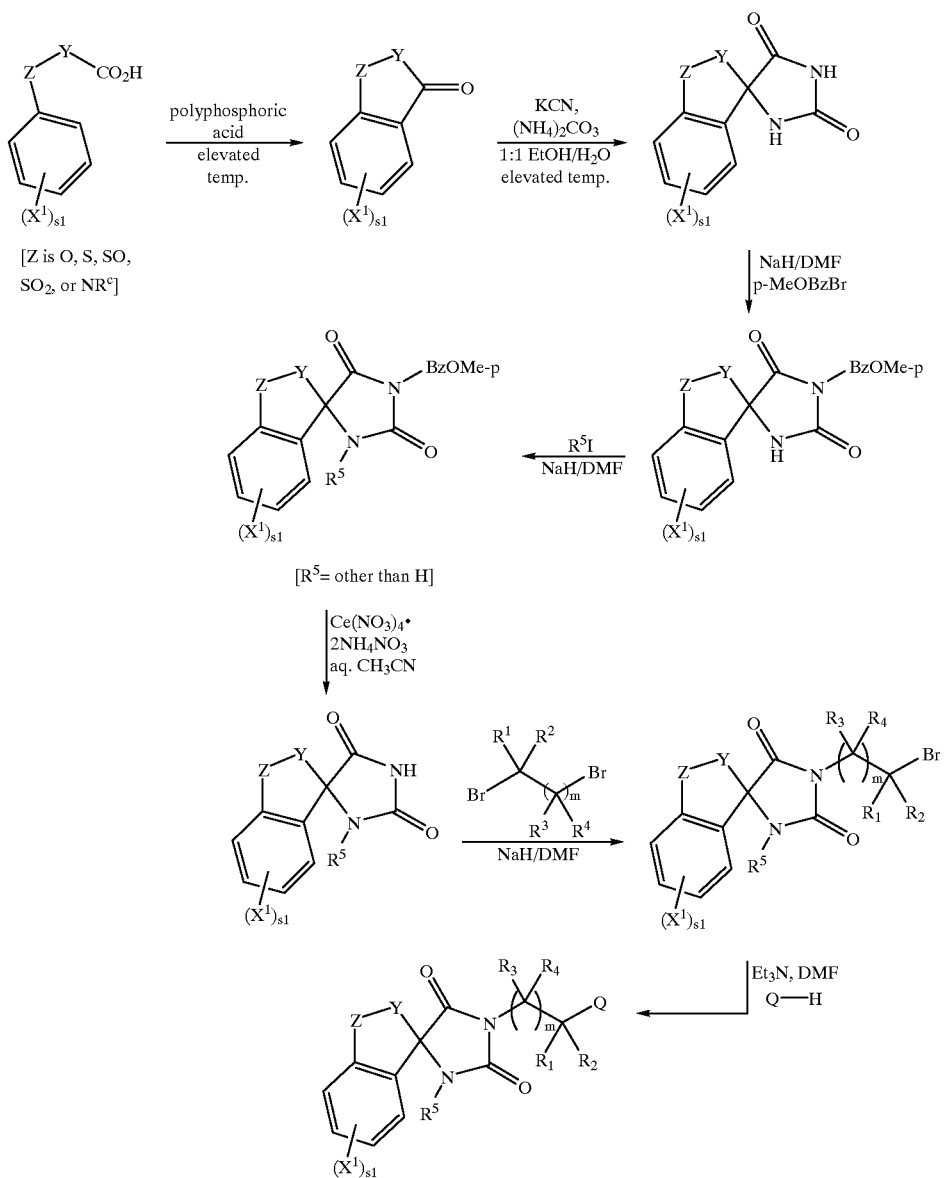

SCHEME 5
A.
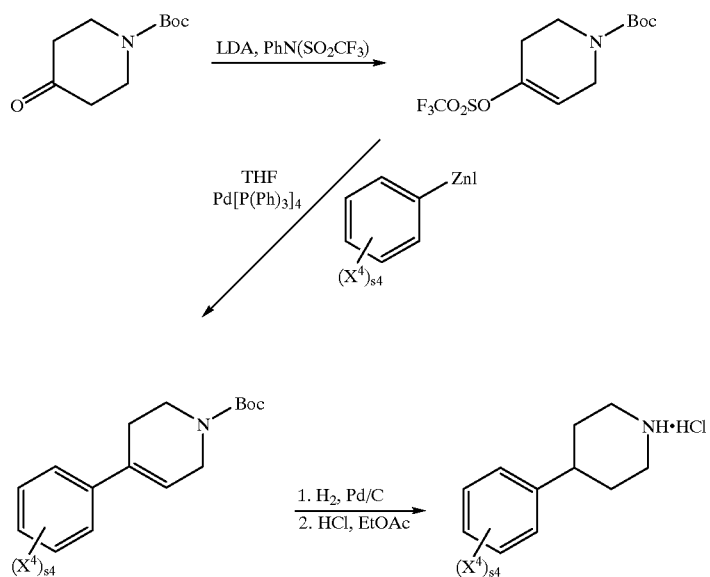
B.
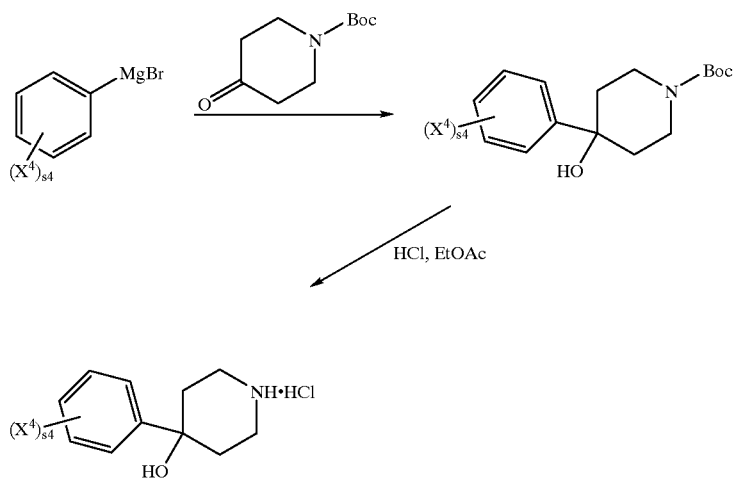
C.
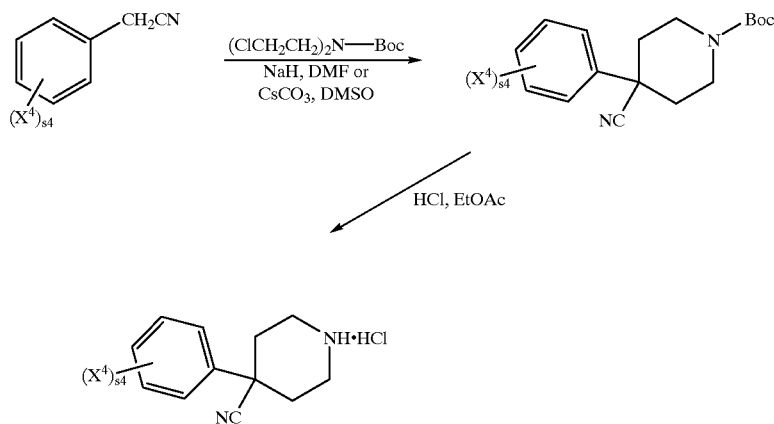

SCHEME 6
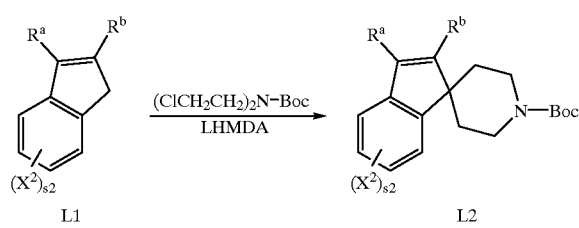
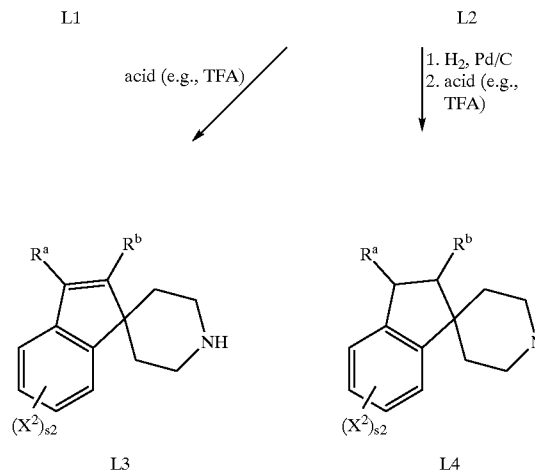
SCHEME 7
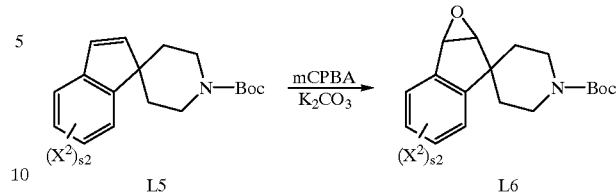
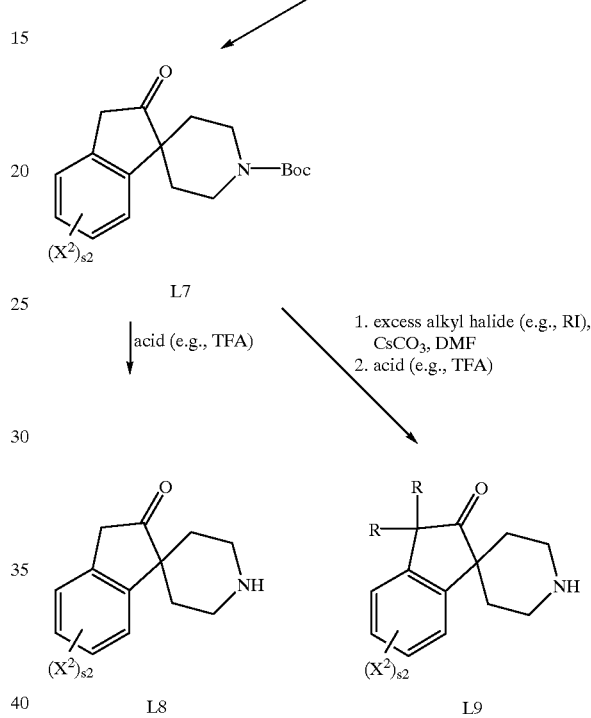
SCHEME 8
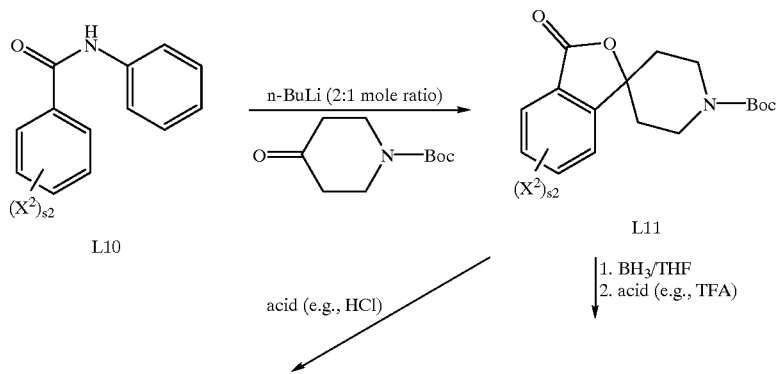

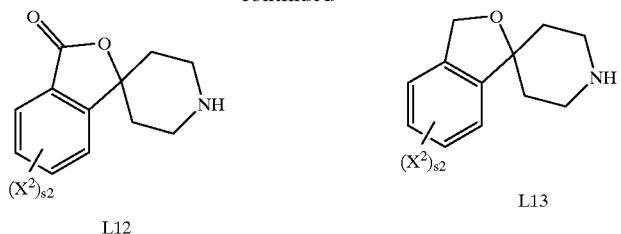
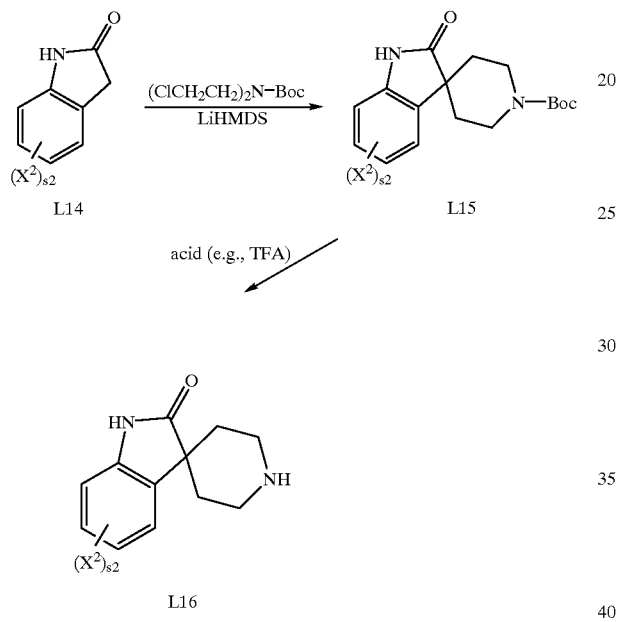
SCHEME 9
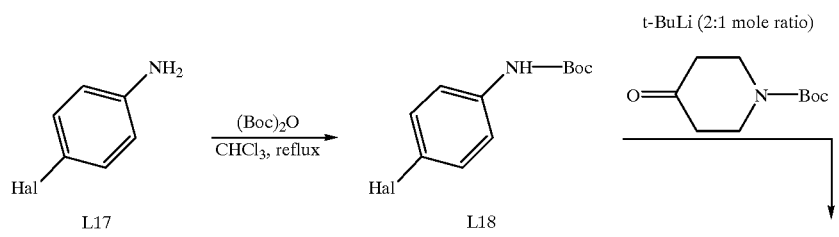
SCHEME 10
[Hal = F or Cl]

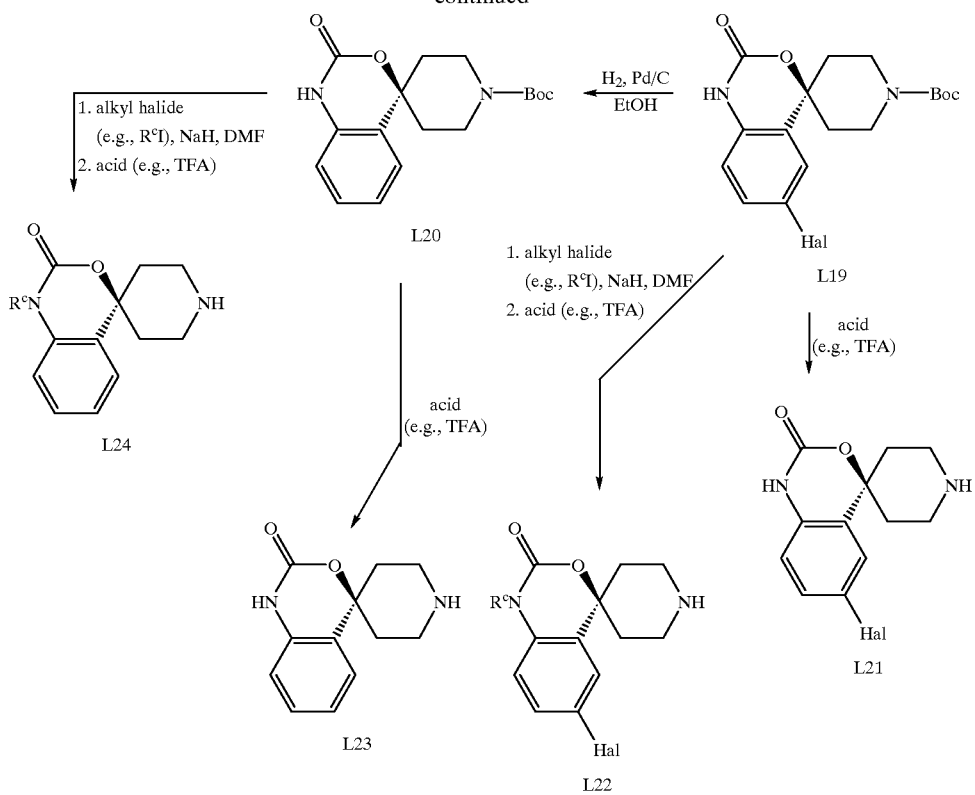

The following examples serve only to illustrate the invention and its practice. The examples are not to be construed as limitations on the scope or spirit of the invention.

EXAMPLE 1

(+/−)-(1), (+)-(2), and (−)-1-{3-[4-(2-Cyano-4-fluorophenyl)piperidin-1-yl]propyl}-5'-fluoro-spiro[imidazolidine-4,1'indan]-2,5-dione hydrochloride (3)

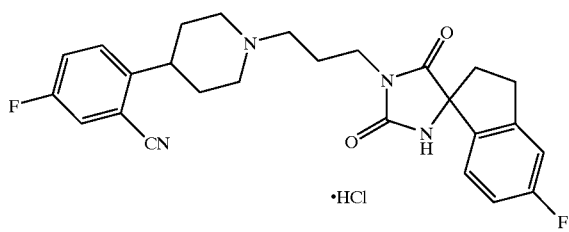

Step A: Preparation of (+/−)-5'-fluoro-spiro[imidazolidine4,1'indan]-2,5-dione

A solution of 5-fluoro-1-indanone (1.5 g, 10.0 mmol) in dimethylformamide (16 mL) and water (1.0 mL) containing potassium cyanide (855 mg., 13 mmol) and ammonium carbonate(3.19 g, 30 mmol) was sealed in a screw-top glass tubular vessel and heated at 130° C. for 24 hours. The cooled reaction vessel was opened and the contents poured into water and acidified with concentrated HCl. The resulting precipitate was collected by filtration, rinsed with water and dried. This solid was digested in ethyl acetate to give purified product as a racemate. m.p.: >260° C.

The enantiomers can be separated by preparative HPLC on a chiral Chiralpak AD column eluting with 20% ethanol and 80% hexane containing 0.1% diethylamine. The first enantiomer to elute was converted to the ultimate product (−)-1'-{3-[4-(2-cyano-4-fluorophenyl)piperidin-1-yl]propyl}-5'-fluoro-spiro[imidazolidine-4,1'indan]-2,5-dione and the second eluent gave (+)-1'-{3-[4-(2-cyano-4-fluorophenyl)piperidin-1-yl]propyl}-5'-fluoro-spiro[imidazolidine-4,1'indan]-2,5-dione Step B: Preparation of (+/−)-1-bromopropyl-5'-fluoro-spiro[imidazolidine-4,1'indan]-2,5-dione

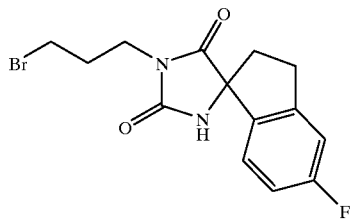

(+/−)-5'-fluoro-spiro[imidazolidine-4,1'indan]-2,5-dione (331 mg.,1.5 mmol) was dissolved in dry dimethylformaride (4 mL) and 60% sodium hydride in mineral oil (72 mg., 1.8 mmol) was added. The mixture was warmed at 50° C for 20 minutes and then 1,3-dibromo-propane (1.1 mL, 10.9 mmol) was added. The reaction mixture was warmed at 50° C. for 2 hours. The cooled reaction mixture was diluted with ethyl acetate and the organic solution was washed with aqueous Na2CO3 and water (3×). The dried extract was evaporated and chromatographed on silica gel using a 10–30% ethyl acetate/hexane gradient. The appropriate fractions were combined and evaporated to give the racemic product as a glassy solid which was used as is.

Step C: Preparation of (+/−)-1-{3-[4-(2-cyano-4-fluorophenyl)piperidin-1-yl]propyl}-5'-fluoro-spiro[imidazolidine-4,1'indan]-2,5-dione hydrochloride A solution of (+/−)-1-bromopropyl-5'-fluoro-spiro[imidazolidine-4,1'indan]-2,5-dione (120 mg, 0.35 mmol) and 4-(2-cyano-4-fluorophenyl)piperidine (78 mg, 0.38 mmol) in dry dimethyl-formamide (2 mL) containing triethylamine (0.07 mL, 0.5 mmol) was warmed at 50° C. for ten hours. The cooled reaction was diluted with ethyl acetate and this solution was washed with aqueous $Na_2CO_3$, water (3×), and then dried over anhydrous $Na_2SO_4$. The filtered extract was evaporated and the residue triturated with cold methanol to give the product as a solid. This solid was suspended in methanol (4 mL) and excess 1M HCl/ether was added to give the hydrochloride salt as a solid. m.p.: >260° C.

Analysis: calculated for C26H26F2N4O2.HCl.0.7 H2O: C, 60.80; H, 5.57; N, 10.91; Found: C, 60.65; H, 5.18; N,10.71.

Step D: Separation of Enantiomers

The racemic (+/−)-1-{3-[4-(2-cyano-4-fluorophenyl)piperidin-1-yl]propyl}-5'-fluoro-spiro[imidazolidine4,1'indan]-2,5-dione hydrochloride was separated by chiral HPLC on a Chiralpak AD column by elution with 20% hexane containing 0.1% diethylamine and 80% ethanol. The first component that eluted was the (+)-enantiomer ([α]$_D$=+16° (CH$_3$Cl) as the HCl salt) and the second was the (−)-enantiomer ([α]$_D$=−16° (CH$_3$Cl) as the HCl salt).

Step E: Alternate Synthesis of (+) and (−)-5'-fluoro-spiro[imidazolidine-4,1'indan]-2,5-dione The racemic 5'-fluoro-spiro[imidazolidine-4,1'indan]-2,5-dione (2.46 gm, 11 mmol) was dissolved in dry dimethylformamide (22 mL) under an argon atmosphere and sodium hydride (477 mg,60% in mineral oil, 12 mmol) was added to form the sodio salt as a clear solution over 30 minutes. (S)-(−)-(α-methylbenzyl isocyanate (2.0 mL, 14 mmol) was then added and the reaction was allowed to stir for 15 hours at ambient temperature. This reaction was acidified with acetic acid(1 equivalent) and diluted with ethyl acetate. The solution was washed with aqueous $Na_2CO_3$, water (3×), dried, filtered and the solvent evaporated. The residue (1.26 gm) was chromatographed on silica gel eluting with a 20–35% ethyl acetate/hexane gradient to separate the two diastereomeric 3-((S)-α-benzylcarbamoyl)-5'-fluoro-spiro[imidazolidine-4,1'indan]-2,5-dione in an overall 17% yield. The more polar diastereomer (326 mg, 0.89 mmol) was dissolved in dry tetrahydrofuran (10 mL) containing anhydrous methanol (0.25 mL, 6 mmol) and sodium hydride (81 mg, 60% in mineral oil, 2 mmol) was added. The reaction was warmed at 60° C. for 2.5 hours and then cooled to ambient temperature. Aqueous 1 N HCl was added to the reaction and the tetrahydrofuran solvent was removed under partial vacuum. The resulting aqueous solution was cooled in a ice bath and acidified with concentrated HCl as the product precipitated out. The collected solid was digested in ethyl acetate to give enantiomerically pure (+)-5'-fluoro-spiro[imidazolidine-4,1'indan]-2,5-dione as determined by comparison on a chiral Chiralpak AD column. The less polar diastereomer can be treated similarly to give the (−)-enantiomer.

EXAMPLE 2

(+/−)(4), (−)(5), and (+)(6)-1'-{3-[4-(4-Fluoro-2-cyanophenyl)piperidin-1-yl]propyl}-7-fluoro-2,3-dihydro-spiro[4H-1-benzopyran-4,4'-imidazolidine]-2',5'-dione hydrochloride

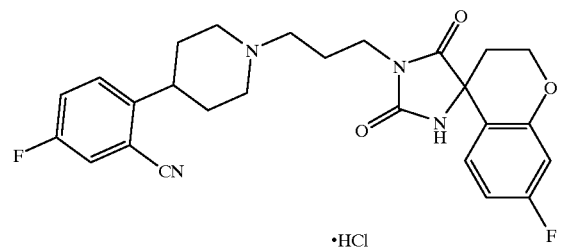

Step A: Preparation of 7-fluoro-2,3-dihydrobenzopyran-4(4H)-one

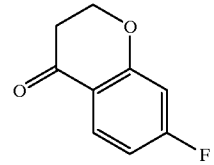

A solution of sodium hydroxide (6.7 gm, 167 mmol) in water (20 mL) was added slowly to a neat mixture of 3-fluorophenol (8.9 gm, 79.5 mmol) and 3-bromopropionic acid (12.26 gm,80 mmol) as the reaction became exothermic. The mixture was refluxed gently for two hours and then allowed to cool and become semi-solid. Water was added to dissolve the semi-solid and then was acidified with concentrated HCl. The product was extracted into diethyl ether and the ethereal extract was dried over anhydrous magnesium sulfate, filtered and evaporated. The residue was slurried in 4:1 hexanetbenzene to give crystalline 3-(3-fluorophenoxy) propionic acid. m.p.: 90–91° C.

A mixture of this phenoxy acid (6.21 gm, 33.8 mmol) and polyphosphoric acid (52 gm) was heated at 120° C. for one hour. The cooled reaction mixture was poured into ice/water and the precipitated product was extracted into diethyl ether. This etheral solution was dried (MgSO4), filtered and evaporated to give a mixture of two isomers which were separated by chromatography on silica gel eluting with a 10–12% ethyl acetate/hexane gradient. The first component was isolated and recrystallized from hexane to give pure 7-fluoro-2,3-dihydrobenzopyran-4(4H)-one. m.p.: 61–62° C. The second component was the 5-fluoro isomer. m.p.:107–109° C.

Step B: Preparation of (+/−) and (−) and (+)-7-fluoro-2,3-dihydro-spiro[4H-1-benzopyran-4,4'-imidazolidine]-2',5'-dione A solution of 7-fluoro-2,3-dihydrobenzopyran-4(4H)-one (830 mg., 5.0 mmol) in ethanol (6 mL) and water (6 mL) containing potassium cyanide (425 mg., 6.5 mmol) and ammonium carbonate(1.44 g, 15 mmol) was sealed in a screw-top glass tubular vessel and heated at 90° C. for 24 hours. The cooled reaction vessel was opened and the contents poured into water and acidified with concentrated HCl. The resulting precipitate was collected by filtration, rinsed with water and dried. This solid was digested in ethyl acetate to give purified product as a racemate. m.p.:>260° C.

The enantiomers were separated by preparative HPLC on a chiral Chiralpak AD column eluting with 20% ethanol and 80% hexane containing 0.1% diethylamine. The first enantiomer to elute was the (−)-enantiomer (250 mg, $[\alpha]_D$=−47° (MeOH) and the second was the (+)-enantiomer (288 mg, $[\alpha]_D$=+46° (MeOH).

Step C: Preparation of (+/−)-1'-(3-bromopropyl)}-7-fluoro-2,3-dihydro-spiro[4H-1-benzopyran4,4'-imidazolidine]-2',5'-dione To a solution of racemic 7-fluoro-2,3-dihydro-spiro[4H-1-benzopyran-4,4'-imidazolidine]-2',5'-dione (236 mg, 1.0 mmol) in dry dimethylformamide (2 mL) was added sodium hydride (64 mg, 60% in mineral oil, 1.6 mmol). This mixture was warmed at 50° C. for ten minutes and then 1,3-dibromopropane (0.71 mL, 7.0 mmol) was added. The reaction was heated at 50° C. for another two hours. The cooled reaction was diluted with ethyl acetate and washed with aqueousNaHCO3, water (3×) and the organic layer was dried(Na2SO4), filtered and the solvent evaporated. The residue was chromatographed on silica gel eluting with a 20–50% ethyl acetate/hexane gradient to give the racemic product as a glassy solid.

Each enantiomer can be prepared similarly starting with the respective enantiomeric (+) or (−)-7-fluoro-2,3-dihydro-spiro[4H-1-benzopyran-4,4'-imidazolidine]-2',5'-dione.

Step D: Preparation of (+/−), (+) and (−)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione hydrochloride A solution of (+/−)-1'-(3-bromopropyl)-7-fluoro-2,3-dihydro-spiro[4H-1-benzopyran-4,4'-imidazolidine]-2',5'-dione (280 mg, 0.78 mmol) and 4-(2-cyano-4-fluorophenyl) piperidine (178 mg, 0.87 mmol) in dry dimethyl-formamide (2.5 mL) containing triethylamine (0.15 mL, 1.1 mmol) was warmed at 50° C. for ten hours. The cooled reaction was diluted with ethyl acetate and this solution was washed with aqueous Na2CO3, water (3×), and then dried over anhydrous Na2SO4. The filtered extract was evaporated and the residue triturated with cold methanol to give the product as a solid. Some of this solid was suspended in methanol (2 mL) and excess 1M HCl/ether was added to give the hydrochloride salt as a solid. m.p.:>250° C.

Analysis: calculated for C26H26F2N4O3.HCl: C, 60.40; H, 5.27; N, 10.84; Found: C, 60.37; H, 5.10; N,10.76.

Each enantiomer can be prepared similarly from the respective enantiomeric 1'-(3-bromopropyl)-7-fluoro-2,3-dihydro-spiro[4H-1-benzopyran-4,4'-imidazolidine]-2',5'-dione. The (+)-enantiomer yielded the (+)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione hydrochloride ($[\alpha]_D$=+37° (CH3Cl)) and the (−)-enantiomer gave the (−)-product as a hydrochloride salt ($[\alpha]_D$=−37° (CH3Cl)).

EXAMPLE 3

The following compounds were prepared in accordance with the procedures set forth in Example 1, Step C, except that that the appropriate piperidine (listed below) was employed instead of 4-(2-cyano-4-fluorophenyl)piperidine.

(+/−)-1-{3-[4-(4-Fluorophenyl)piperidin-1-yl] propyl}-5'-fluoro-spiro[imidazolidine-4,1'indan]-2,5-dione hydrochloride (7)

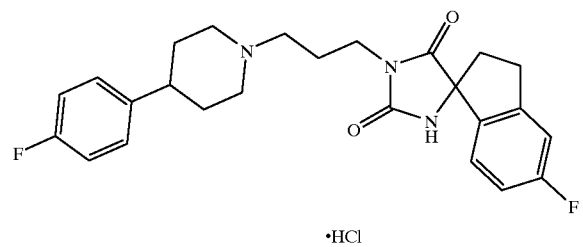

·HCl piperidine: 4-(4-fluorophenyl)piperidine; m.p.: 226–229° C.; Analysis: calculated for C25H27F2N3O2.HCl.0.45 H2O: C, 62.05; H, 5.88; N, 8.70; Found: C, 62.03; H, 6.02; N, 8.68.

(+/−)-1-{3-[4-Cyano-4-phenyl-piperidin-1-yl] propyl}-5'-fluoro-spiro[imidazolidine-4,1'indan]-2,5-dione hydrochloride (8)

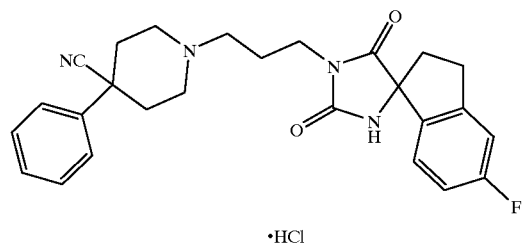

·HCl piperidine: 4-cyano-4-phenylpiperidine; m.p.: >180° C.; slowly shrinks; Analysis: calculated for C26H27FN4O2.HCl.0.45 H2O: C, 63.58; H, 5.93; N, 11.41; Found: C, 63.63; H, 5.93; N, 11.31.

The racemate was separated into the enantiomers via chiral HPLC. The optical rotation of the isomers was not measured. The first enantiomer to elute is referred to herein as compound 9, and the second to elute as compound 10.

(+/−)-1-{3-[4-(4-Cyano-4-(2-cyanophenyl))piperidin-1-yl]propyl}-5'-fluoro-spiro[imidazolidine-4,1'indan]-2,5-dione hydrochloride (11)

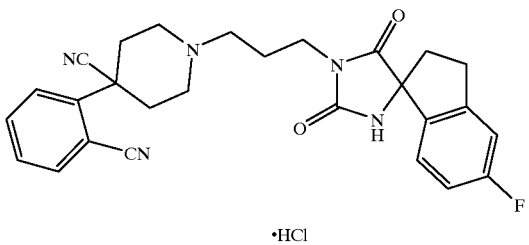

•HCl piperidine: 4-(4-cyano-4-(2-cyanophenyl))piperidine; m.p.: 261–263° C.; Analysis: calculated for $C_{27}H_{26}FN_5O_2 \cdot HCl$: C, 63.83; H, 5.36; N, 13.79; Found: C, 63.54; H, 5.16; N, 13.80.

(+/−)-1-{3-{Spiro[indano-1,4'-piperidin]-1-yl}propyl}-5'-fluoro-spiro[imidazoline-4,1'indan]-2,5-dione hydrochloride (12)

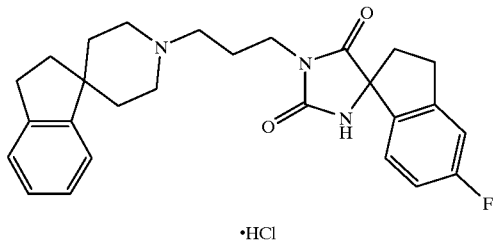

•HCl piperidine: spiro(indano-1,4'-piperidine); m.p.: 259–260° C.; Analysis: calculated for $C_{27}H_{30}FN_3O_2 \cdot HCl$: C, 67.00; H, 6.46; N, 8.68; Found: C, 66.97; H, 6.38; N, 8.86.

The racemate was separated into the enantiomers via chiral HPLC. The optical rotation of the isomers was not measured. The first enantiomer to elute is referred to herein as compound 13, and the second to elute as compound 14.

(+/−)-1-{3-{6-Chlorospiro[4H-3,1-benzoxazine-4,4'-piperidin]-2(1H)-on-1'-yl}propyl}-5'-fluoro-spiro[imidazolidine-4,1'indan]-2,5-dione hydrochloride (15)

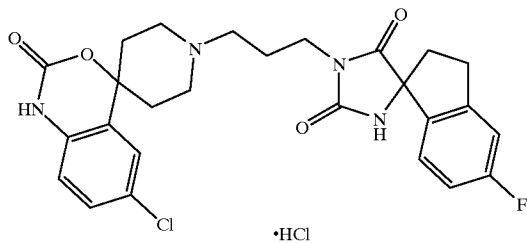

•HCl piperidine: 6-chlorospiro[4H-3,1-benzoxazine-4,4'-piperidin]-2(1H)-one; m.p.: >205° C.; slowly shrinks; Analysis: calculated for $C_{26}H_{26}ClFN_4O_4 \cdot HCl \cdot 0.45 H_2O$: C, 56.01; H, 5.04; N, 10.05; Found: C, 56.03; H, 5.16; N, 10.27.

EXAMPLE 4

The following compounds were prepared in accordance with the procedures set forth in Example 1, except that the appropriate indanone and piperidine (listed below) were employed in Steps A and C respectively instead of one or both of 5-fluoroindanone and 4-(2-cyano-4-fluorophenyl)piperidine.

(+/−)-1-{3-[4-Cyano-4-phenyl-piperidin-1-yl]propyl}-6'-fluoro-spiro[imidazolidine-4,1'indan]-2,5-dione hydrochloride (16)

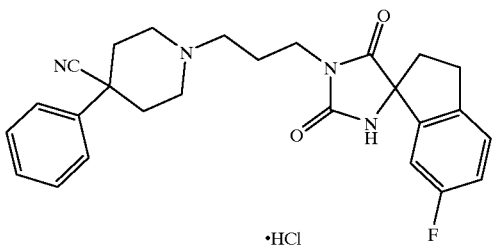

•HCl indanone: 6-fluoroindanone; piperidine: 4-cyano-4-phenylpiperidine; m.p.: >260° C.; Analysis: calculated for $C_{26}H_{27}FN_4O_2 \cdot HCl$: C, 64.64; H, 5.89; N, 11.52; Found: C, 64.65; H, 5.84; N, 11.60.

(+/−)-1-{3-{Spiro[indano-1,4'-piperidine]-1-yl}propyl}-6'-fluoro-spiro[imidazolidine-4,1'indan]-2,5-dione hydrochloride (17)

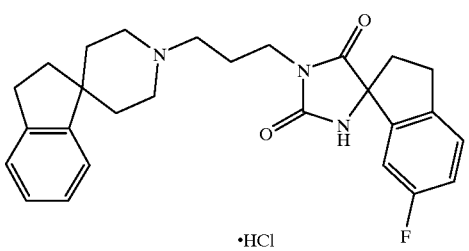

•HCl indanone: 6-fluoroindanone; piperidine: spiro[indano-1,4'-piperidine]; m.p.: 233–235° C.; Analysis: calculated for $C_{27}H_{30}FN_3O_2 \cdot HCl \cdot 0.25 H_2O$: C, 66.38; H, 6.50; N, 8.60; Found: C, 66.41; H, 6.50; N, 8.63.

(+/−)-1-{3-[4-(4-Fluoro-2-cyanophenyl)piperidin-1-yl]propyl}-5',6'-difluoro-spiro[imidazolidine-4,1'indan]-2,5-dione hydrochloride (18)

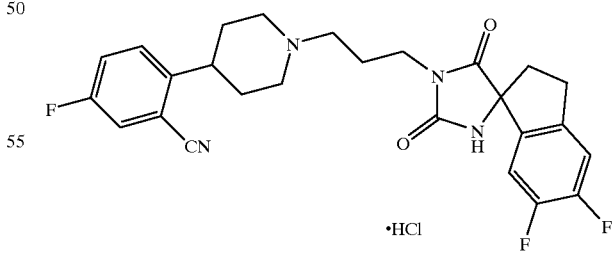

•HCl indanone: 5,6,-difluoroindanone; piperidine: 4-(4-fluoro-2-cyanophenyl)piperidine; m.p.: >260° C.; Analysis: calculated for $C_{26}H_{25}F_3N_4O_2 \cdot HCl$: C, 60.17; H, 5.05; N, 10.80; Found: C, 60.11; H, 5.05; N, 10.66.

The racemate was separated into the enantiomers via chiral HPLC. The optical rotation of the isomers was not measured. The first enantiomer to elute is referred to herein as compound 19, and the second to elute as compound 20.

(+/−)-1-{3-{spiro[indano-1,4'-piperidin]-1-yl}propyl}-5',6'-difluoro-spiro[imidazolidine-4,1'indan]-2,5-dione hydrochloride (21)

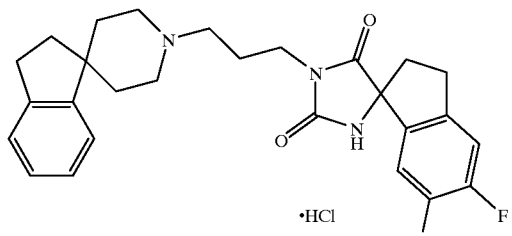

indanone: 5,6-difluoroindanone; piperidine: spiro[indano-1,4'-piperidine]; m.p.: 210–212° C.; Analysis: calculated for C27H29FN3O2.HCl: C, 64.60; H, 6.02; N, 8.37; Found: C, 65.00; H, 5.79; N, 8.24.

(+/−)-1-{3-[4-(4-Fluorophenyl)piperidin-1-yl]propyl}-5'-chloro-spiro[imidazolidine-4,1'indan]-2,5-dione hydrochloride (22)

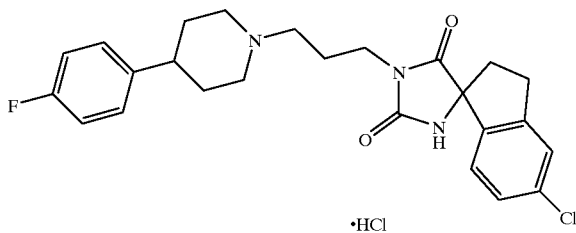

indanone: 5-chloroindanone; piperidine: 4-(4-fluorophenyl)piperidine; m.p.: 251–254° C.; Analysis: calculated for C25H27ClFN3O2.HCl: C, 60.98; H, 5.73; N, 8.53; Found: C, 60.90; H, 5.66; N, 8.36.

(+/−)-1-{3-[4-(4-Fluoro-2-cyanophenyl)piperidin-1-yl]propyl}-5'-chloro-spiro[imidazolidine-4,1'indan]-2,5-dione hydrochloride (23)

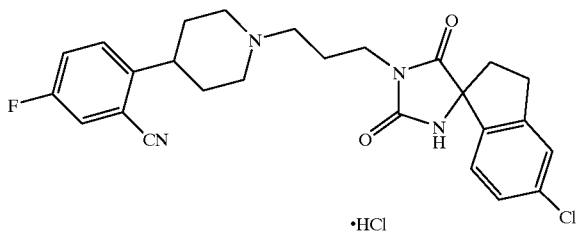

indanone: 5-chloroindanone; piperidine: 4-(4-fluoro-2-cyanophenyl)piperidinine; m.p.: >260° C.; Analysis: calculated for C26H26ClFN4O2.HCl.0.20 H2O: C, 59.93; H, 5.30; N, 10.75; Found: C, 59.94; H, 5.26; N, 10.70.

The racemate was separated into the enantiomers via chiral HPLC. The optical rotation of the isomers was not measured. The first enantiomer to elute is referred to herein as compound 24, and the second to elute as compound 25.

(+/−)-1-{3-{Spiro[indano-1,4'-piperidin]-1-yl}propyl}-5'-chloro-spiro[imidazolidine-4,1'indan]-2,5-dione hydrochloride (26)

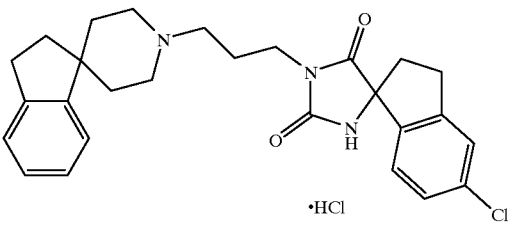

indanone: 5-chloroindanone; piperidine: spiro[indano-1,4'-piperidine]; m.p.: >260° C.; Analysis: calculated for C27H30ClN3O2.HCl: C, 64.80; H, 6.24; N, 8.40; Found: C, 64.53; H, 6.17; N, 8.38.

The racemate was separated into the enantiomers via chiral HPLC. The optical rotation of the isomers was not measured. The first enantiomer to elute is referred to herein as compound 27, and the second to elute as compound 28.

(+/−)-1-{3-{6-Chlorospiro[4H-3,1-benzoxazine-4,4'-piperidin]-2(1H)-on-1'-yl}propyl}-5'-chloro-spiro[imidazolidine-4,1'indan]-2,5-dione hydrochloride (29)

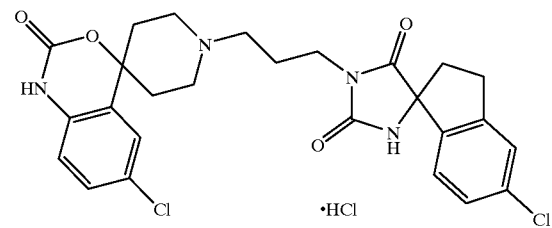

indanone: 5-chloroindanone; piperidine: 6-chlorospiro[4H-3,1-benzoxazine-4,4'-piperidin-2(1H)-one]; m.p.: 231–234° C.; Analysis: calculated for C26H26Cl2N4O4.HCl.0.30 H2O: C, 54.66; H, 4.87; N, 9.81; Found: C, 54.65; H, 4.81; N, 9.49.

(+/−)-1-{3-[4-(2-pyridinyl)piperidin-1-yl]propyl}-5'-chloro-spiro[imidazoline-4,1'indan]-2,5-dione hydrochloride (30)

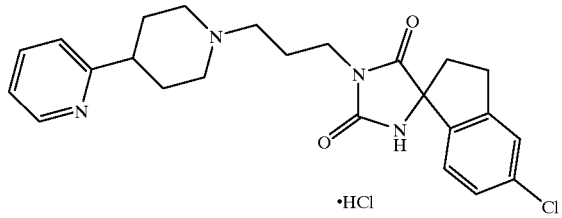

indanone: 5-chloroindanone; piperidine: 4-(2-pyridinyl)piperidine; m.p.: 251–253° C.; Analysis: calculated for C24H27ClN4O2.HCl.0.20 H2O: C, 55.92; H, 5.75; N, 10.87; Found: C, 55.89; H, 5.72; N, 10.68.

(+/−)-1-{3-{Spiro[indano-1,4'-piperidin]-1-yl}propyl}-6'-chloro-spiro[imidazolidine-4,1'indan]-2,5-dione hydrochloride (31)

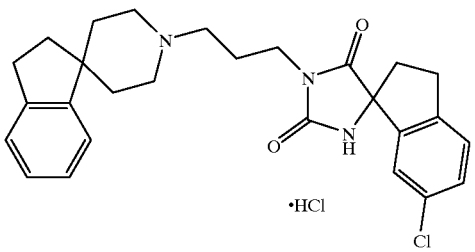

indanone: 6-chloroindanone; piperidine: spiro[indano-1,4'-piperidine]; m.p.: 246–248° C.; Analysis: calculated for C27H30ClN3O2.HCl.0.25 H2O: C, 64.21; H, 6.29; N, 8.32; Found: C, 64.20; H, 6.29; N, 8.27.

(+/−)-1-{3-{Spiro[indano-1,4'-piperidin]-1-yl}propyl}-4'-methyl-spiro[imidazoline-4,1'indan]-2,5-dione hydrochloride (32)

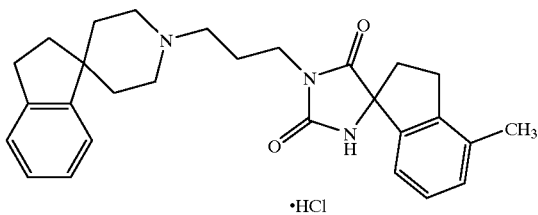

indanone: 4-methylindanone; piperidine: spiro[indano-1,4'-piperidine]; m.p.: >260° C.; Analysis: calculated for C28H33N3O2.HCl.0.20 H2O: C, 69.53; H, 7.17; N, 8.69; Found: C, 69.52; H, 7.03; N, 8.66.

(+/−)-1-{3-{Spiro[indano-1,4'-piperidin]-1-yl}propyl}-5'-methyl-spiro[imidazolidine-4,1'indan]-2,5-dione hydrochloride (33)

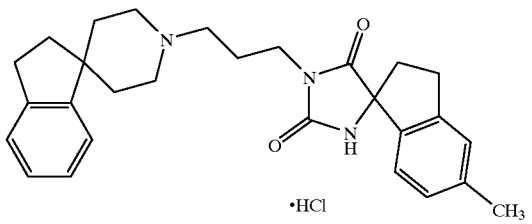

indanone: 5-methylindanone; piperidine: spiro[indano-1,4'-piperidine]; m.p.: 230–232° C.; Analysis: calculated for C28H33N3O2.HCl.0.40 H2O: C, 69.01; H, 6.80; N, 8.54; Found: C, 69.01; H, 7.20; N, 8.62.

The racemate was separated into the enantiomers via chiral HPLC. The first enantiomer to elute (34) had an optical rotation of ([α]$_D$=−9.1 (CHCl$_3$)). m.p.:242–244° C. The second isomer to elute (35) had an optical rotation of ([α]$_D$=+7.1° (CHCl$_3$)). m.p.: 241–243° C.

(+/−)-1-{3-[4-(4-Fluoro-2-cyanophenyl)piperidin-1-yl]propyl}3-5'-methyl-spiro[imidazolidine-4,1'indan]-2,5-dione hydrochloride (36)

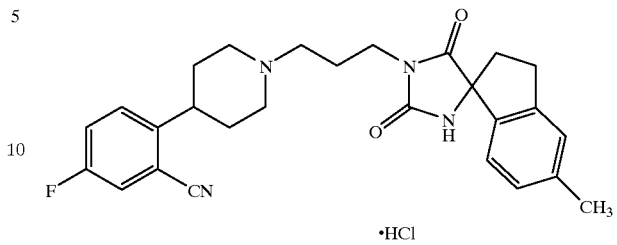

indanone: 5-methylindanone; piperidine: 4-(4-fluoro-2-cyanophenyl)piperidine; m.p.: >260° C.; Analysis: calculated for C27H29FN4O2.HCl: C, 65.25; H, 6.08; N, 11.29; Found: C, 65.12; H, 6.38; N, 11.40.

The racemate was separated into the enantiomers via chiral HPLC. The optical rotation of the isomers was not measured. The first enantiomer to elute is referred to herein as compound 37, and the second to elute as compound 38.

(+/−)-1-{3-{Spiro[indano-1,4'-piperidin]-1-yl}propyl}-6'-methyl-spiro[imidazolidine-4,1'indan]-2,5-dione hydrochloride (39)

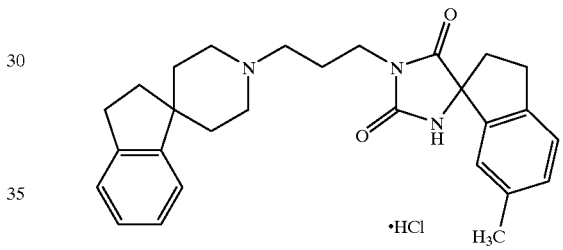

indanone: 6-methylindanone; piperidine: spiro[indano-1,4'-piperidine]; m.p.: 251–253° C.; Analysis: calculated for C28H33N3O2.HCl: C, 70.05; H, 7.14; N, 8.75; Found: C, 70.05; H, 7.09; N, 8.55.

(+/−)-1-{3-[4-Cyano-4-phenyl-piperidin-1-yl]propyl}-3-fluoro-spiro[9H-fluorene-9,4'-imidazolidine]-2',5'-dione hydrochloride (40)

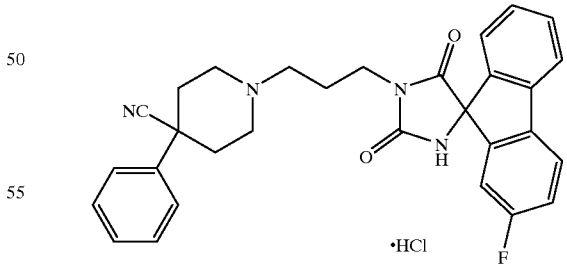

indanone: 3-fluorenone; piperidine: 4-cyano-4-phenylpiperidine; m.p.: >260° C.; Analysis: calculated for C30H27FN4O2.HCl: C, 67.85; H, 5.31; N, 10.55; Found: C, 67.66; H, 5.30; N, 10.44.

EXAMPLE 5

The following compounds were prepared in accordance with the procedures set forth in Example 2, except that the appropriate cyclic ketone and piperidine (listed below) were employed in Steps B and D respectively instead of one or both of 7-fluoro-2,3-dihydrobenzopyran-4(4H)-one and 4-(4-fluorophenyl)-piperidine.

(+/−)-1'-{3-[4-(4-Fluorophenyl)piperidin-1-yl]propyl}-7-fluoro-2,3-dihydro-spiro[4H-1-benzopyran-4,4'-imidazolidine]-2',5'-dione hydrochloride (41)

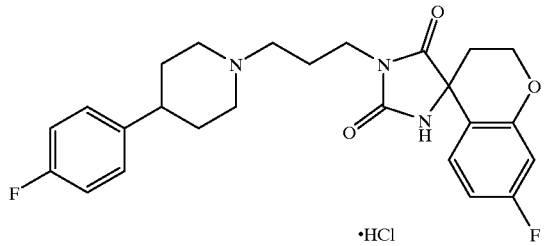

ketone: 7-fluoro-2,3-dihydrobenzopyran-4(4H)-one; piperidine: 4-(4-fluorophenyl)-piperidine; m.p.: >260° C.; Analysis: calculated for C30H27FN4O2.HCl.0.20 H2O: C, 60.83; H, 5.39; N, 8.51; Found: C, 60.81; H, 5.69; N, 8.34.

The racemate was separated into the enantiomers via chiral HPLC. The first enantiomer to elute (42) had an optical rotation of ($[\alpha]_D$=+66.70 (CHCl$_3$)). The second isomer to elute (43) had an optical rotation of ($[\alpha]_D$=−39.10 (CHCl$_3$)).

(+/−)-1'-{3-[4-(4-Fluoro-2-cyanophenyl)piperidin-1-yl]propyl}-7-chloro-2,3-dihydro-spiro[4H-1-benzopyran-4,4'-imidazolidine]-2',5'-dione hydrochloride (44)

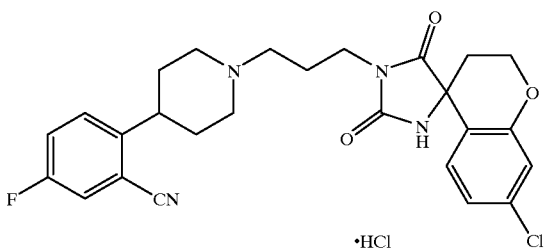

ketone: 7-chloro-2,3-dihydrobenzopyran-4(4H)-one; piperidine: 4-(4-fluoro-2-cyanophenyl)-piperidine; m.p.: >260° C.; Analysis: calculated for C26H26ClFN4O3.HCl: C, 58.54; H, 5.10; N, 10.51; Found: C, 58.77; H, 5.02; N, 10.35.

(+/−)-1'-{3-[4-(4-Fluoro-2-cyano-phenyl)piperidin-1-yl]propyl}-7-fluoro-2,3-dihydro-spiro[4H-1-benzothiopyran-4,4'-imidazolidine]-2',5'-dione hydrochloride (45)

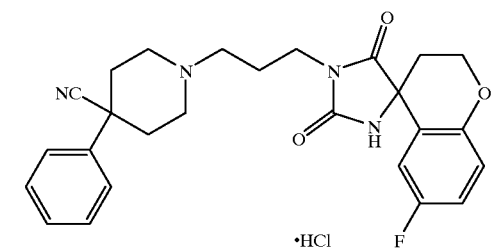

ketone: 7-fluoro-2,3-dihydrobenzothiopyran-4(4H)-one; piperidine: 4-(4-fluoro-2-cyanophenyl)-piperidine; m.p.: >260° C.; Analysis: calculated for C26H26F2N4O2S.HCl.0.20 H2O: C, 58.09; H, 5.16; N, 10.42; Found: C, 58.09; H, 4.94; N, 10.19.

(+/−)-1'-{3-[4-(4-Fluoro-2-cyano-phenyl)piperidin-1-yl]propyl}-7-fluoro-2,3-dihydro-1,1-dioxo-spiro[4H-1-benzothio-pyran-4,4'-imidazolidine]-2',5'-dione hydrochloride (46)

ketone: 7-fluoro-2,3-dihydro-1,1-dioxo-benzothiopyran-4(4H)-one; piperidine: 4-(4-fluoro-2-cyanophenyl)-piperidine; m.p.: >260° C.; Analysis: calculated for C26H26F2N4O4S.HCl: C, 55.26; H, 4.82; N, 9.92; Found: C, 55.24; H, 4.75; N, 9.77.

(+/−)-1'-[3-(4-Cyano-4-phenylpiperidin-1-yl)propyl]-6-fluoro-2,3-dihydro-spiro[4H-1-benzopyan-4,4'-imidazolidine]-2',5'-dione hydrochloride (47)

ketone: 6-fluoro-2,3-dihydrobenzopyran-4(4H)-one; piperidine: 4-cyano-4-phenylpiperidine; m.p.: >260° C.; Analysis: calculated for C30H27FN4O2.HCl.0.20 H2O: C, 62.13; H, 5.70; N, 11.15; Found: C, 62.16; H, 5.61; N, 11.10.

(+/−)-1'-[3-(4-Cyano-4-phenylpiperidin-1-yl) propyl]-3-fluoro-6,7,8,9-tetrahydro-spiro[5H-benzocycloheptene-5,4'-imidazolidine]-2',5'-dione hydrochloride (48)

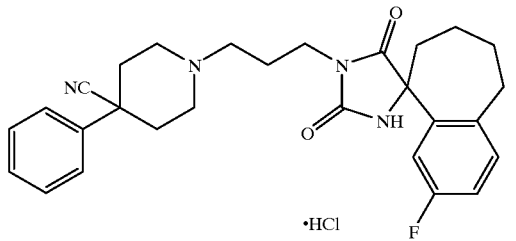

ketone: 3-fluorobenzocycloheptanone; piperidine: 4-cyano-4-phenylpiperidine; m.p.: >260° C.; Analysis: calculated for C28H31FN4O2.HCl.0.25 H2O: C, 65.23; H, 6.35; N, 10.87; Found: C, 65.17; H, 6.26; N, 10.87;

(+/−)-1'-{3-[4-(4-Fluoro-2-cyano-phenyl)piperidin-1-yl]propyl}-6-fluoro-2,3-dihydro-spiro[1-benzofuran-3(2H),4'-imidazolidine]-2',5'-dione hydrochloride (49)

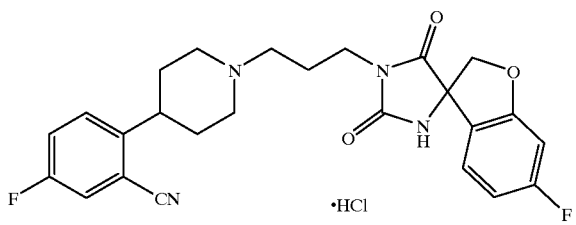

ketone: 6-fluoro-2,3-dihydrobenzofuran-3(2H)-one; piperidine: 4-(4-fluoro-2-cyanophenyl)piperidine; m.p.: >250° C.; Analysis: calculated for C25H24F2N4O3.HCl: C, 59.70; H, 5.07; N, 11.14; Found: C, 59.45; H, 5.37; N, 11.63.

(+/−)-1-{3-[4-(4-fluoro-2-cyano-phenyl)piperidin-1-yl]propyl}-8-fluoro-2,3,4,5-tetrahydro-spiro[1-benzoxepin-5(2H),4'-imidazolidine]-2',5'-dione hydrochloride (50)

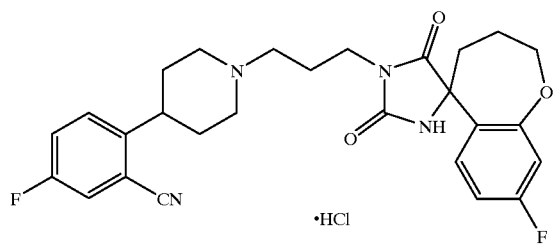

ketone: 8-fluoro-2,3,4,5-tetrahydrobenzoxepin-5(2H)-one; piperidine: 4-(4-fluoro-2-cyanophenyl)piperidine; m.p.: >140° C. slowly shrinks; Analysis: calculated for C27H28F2N4O3.HCl.1.30 H2O: C, 58.49; H, 5.75; N, 10.11; Found: C, 58.45; H, 5.55; N, 10.05.

EXAMPLE 6

(+/−)-1-{3-[4-(4-fluorophenyl)piperidin-1-yl]butyl}-5'-chloro-spiro[imidazolidine-4,1'indan]-2,5-dione hydrochloride (mixture of 4 diastereomers) (51)

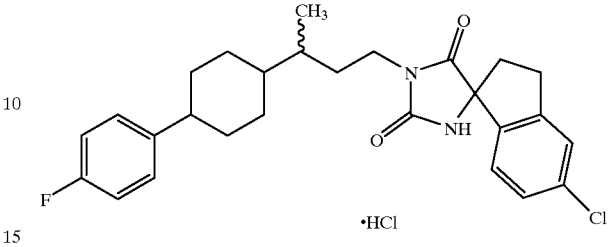

Step A: Preparation of (+/−)-5'-chloro-spiro[imidazolidine-4,1'indan]-2,5-dione

The title compound was prepared according to the procedure of Example 1, Step A, except substituting 5-chloro-1-indanone for 5-fluoro-1-indanone in 83% yield, mp: >250° C., as a racemate.

Step B: Preparation of (+/−)-1-amino-5-chloro-indane-1-carboxylic acid

A mixture of (+/−)-5'-chloro-spiro[imidazolidine-4,1'indan]-2,5-dione (473 mg, 2 mmol) in water (55 mL) containing barium hydroxide nonahydrate (3.06 gm, 10 mmol) was sealed in a screw-top vessel and heated at 120° C. for 22 hours. The reaction suspension was cooled, the vessel opened and the mixture diluted to ~200 mL with water. This suspension was brought to boil and small pieces of solid carbon dioxide were added over a 1–2 hour period. The heat was removed and the suspension was filtered while still very warm. The aqueous filtrate was concentrated under vacuum and the residue redissolved in water (30 mL). A few drops of sulfuric acid were added and any suspended material removed by filtration before concentrating the aqueous solution to dryness. This residue was triturated with methanol and several crops of the crude title compound were obtained. This material was used as is.

Step C: Preparation of (+/−)-1-tert-butoxycarbonylamino-5-chloro-indane-1-carboxylic acid To a solution of (+/−)-1-amino-5-chloro-indane-1-carboxylic acid (292 mg, 1.38 mmol) in water (4 mL) and tetrahydrofuran (8 mL) containing triethylamine (0.2 mL, 1.43 mmol) was added di-tert-butyl dicarbonate (370 mg, 1.7 mmol). The reaction mixture was stirred at ambient temp. for 18 hours and then diluted with ethyl acetate. Dilute aqueous hydrochoric acid was added and the organic layer separated, dried (anhydrous sodium sulfate), and filtered and the solvent concentrated under vacuum. The residue was triturated with hexane to give the crystalline title compound.

Step D: Preparation of (+/−)-l-(1-cyano-2-propyl)-4-(4-fluorophenyl)piperidine

A solution of 4-(4-fluorophenyl)piperidine (360 mg, 2 mmol) and crotononitrile (0.33 mL, 4 mmol) in methanol (4 mL) was refluxed for five hours. The solvent was concentrated under vacuum and the residue triturated with hexane/diethyl ether to give the racemic title compound as a solid.

Step E: Preparation of (+/−)-1-(1-amino-3-butyl)-4-(4-fluorophenyl)piperidine

A solution of (+/−)-1-(1-cyano-2-propyl)-4-(4-fluorophenyl)piperidine (457 mg, 1.85 mmol) in tetrahydrofuran (5 mL) was added dropwise to 1 M borane/tetrahydrofuran (5 mL) under an inert argon atmosphere. The reaction mixture was refluxed for two hours and then cooled to ambient temperature. 6 N HCl (4 mL) was added to the reaction, stirred for 0.5 hour and then the tetrahydrofuran boiled off. The resultant aqueous solution was cooled in an ice bath and made basic by addition solid sodium hydroxide pellets. The product was extracted into methylene chloride, the extract dried (anhydrous sodium sulfate), filtered, and the solvent removed to give the title compound as a colorless oil.

Step F: Preparation of (+/−)N-{3-[4-(4-fluorophenyl)piperidin-1-yl]butyl}-1-tert-butoxycarbonylamino-5-chloro-indane-1-carboxamide To a solution of (+/−)-1-(1-amino-3-butyl)-4-(4-fluorophenyl)piperidine (316 mg, 1.26 mmol) in anhydrous dimethylformamide (5 mL) was added, in sequence, (+/−)-1-tert-butoxycarbonyl-amnino-5-chloro-indane-1-carboxylic acid (281 mg, 0.90 mmol), 1-hydroxybenzotriazole hydrate (142 mg, 1 mmol), triethylamine (0.35 mL, 2.5 mmol), and 1-ethyl-3-(3-dimethylaminopropyl)-carboduimide hydrochloride (233 mg, 1.2 mmol).This reaction mixture was stirred at room temperature for 22 hours and then diluted with ethyl acetate. The organic layer was separated and washed with water (3×), dried (anhyd. sodium sulfate), filtered and the solvent concentrated under vacuum. The residue was subjected to a column chromatography on silica gel eluting with a 50–100% ethyl acetate/hexane gradient followed by a 1–1.5% methanol/ethyl acetate gradient. The appropriate fractions were combined and concentrated to give the title compound as a viscous oil.

Step G: Preparation of (+/−)-1-{3-[4-(4-fluorophenyl)piperidin-1-yl]butyl}-5'-chloro-spiro[imidazolidine-4,1'indan]-2,5-dione hydrochloride To a solution of (+/−)N-{3-[4-(4-fluorophenyl)piperidin-1-yl]butyl}-1-tert-butoxycarbonylamino-5-chloro-indane-1-carboxamide (170 mg, 0.31 mmol) in tetrahydrofuran (4 mL) was added 60% sodium hydride/mineral oil (30 mg, 0.7 mmol) and the reaction mixture was warmed at 50° C. for one hour. The cooled reaction was diluted with ethyl acetate, washed with aqueous sat'd sodium bicarbonate, dried (anhyd. sodium sulfate), filtered, and the solvent concentrated under vacuum. The residue was triturated with methanol and the solid product collected by filtration. This material was suspended in methanol (3 mL) and 1 HCl/diethyl ether (0.25 mL) was added. Upon dilution with more diethyl ether the product salt slowly precipitated and solidified to give the title compound. By chiral HPLC this is a mixture of at least three diastereomers.

m.p.: >170° C. slowly shrinks; Analysis: calculated for $C_{26}H_{29}ClFN_3O_2 \cdot HCl \cdot 0.70 H_2O$: C, 60.16; H, 6.10; N, 8.10; Found: C, 60.20; H, 5.98; N, 8.03.

EXAMPLE 7

As a specific embodiment of an oral composition, 100 mg of the (+)-enantiomer of Example 1 (i.e., compound 2) is formulated with sufficient finely divided lactose to provide a total amount of 580 to 590 mg to fill a size O hard gel capsule.

EXAMPLE 8

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 $\mu$l) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 9

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 $\mu$l) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

All of the compounds of the present invention prepared in Examples 1–6 were found to have alpha 1a Ki values of less than about 511 nM, as determined via the screening assay described in Example 8. The following compounds were found to have alpha 1a Ki values of less than about 100 nM: 1–8, 10–12, 14,15, 17–26, 28–33, 35–39 and 41–51.

All of the compounds exhibited selectivity for the alpha 1a receptor with respect to both the alpha 1b and alpha 1d receptors. The following compounds were found to be at least about 10-fold more selective in binding to alpha 1a receptors versus binding to the alpha 1b and alpha 1d receptors: 1–8, 10–12, 14,15, 17–19, 21–26, 28–33, 35–39, 41–46, 48, 50 and 51.

The following compounds were found to have alpha 1a Ki values of less than about 10 nM and also found to be at least about 40-fold more selective in binding to alpha 1a receptors versus binding to the alpha 1b and alpha 1d receptors: 1–6, 10, 12, 14, 18, 19, 21, 23, 24, 26, 28, 29, 33, 35, 36, 37, 42, 45 and 50.

EXAMPLE 10

Counterscreen: Histamine-1 Selectivity

The binding affinity (Ki in nM) of the compounds of the present invention for histamine H1 receptors can determined via the binding assay described in Chang et al., *J. Neurochem.* (1979), 32: 1653, or as described in U.S. Pat. No. 5,403,847, or suitable modifications thereof known to those skilled in the art. The assay can be used to eliminate agents which specifically affect binding to hH1 receptors.

EXAMPLE 11

Exemplar Counter Screens
1. Assay Title: Dopamine D2, D3, D4 in vitro screen
Objective of the Assay:

The objective of this assay is to eliminate agents which specifically affect binding of [3H] spiperone to cells expressing human dopamine receptors D2, D3 or D4.
Method:

Modified from VanTol et al., *Nature* (1991), 350: 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 5.0 mM Tris-HCl pH 7.4.

2. Assay Title: Serotonin 5HT1a
Objective of the Assay

The objective of this assay is to eliminate agents which specifically affect binding to cloned human 5HT1a receptor
Method:

Modified from Schelegel and Peroutka, *Biochemical Pharmacology* (1986), 35: 1943–1949.

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/Cfilters

EXAMPLE 12

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_{2/95}$% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (-log $K_b$) values were obtained from Schild plot when three or more concentrations were tested. When less than three concentrations of antagonist are tested, $K_b$ values are calculated according to the following formula $K_b=[B]/x-1$, where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLHIT software package) with a four parameter logistic equation constraining the slope, minimum response, and maximum response to be constant among curves. The dose ratios for the antagonist doses (rightward shift in the dose-response curves from control) are calculated as the ratio of the ED50's for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of formula:

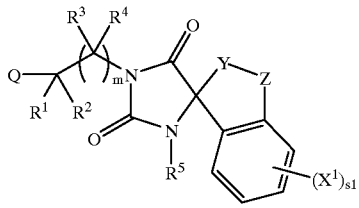

wherein Q is

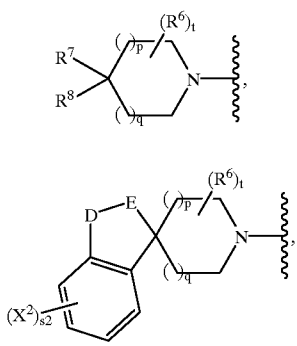

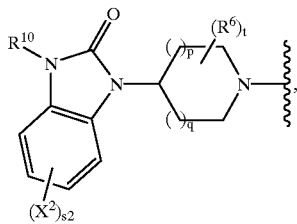

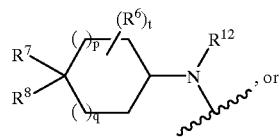

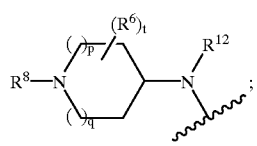

$R^1$, $R^2$, $R^3$ and $R^4$ are each independently selected from hydrogen, fluorine, $C_1$–$C_6$ alkyl, and $C_3$–$C_8$ cycloalkyl;

$R^5$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $(CH_2)_{1-4}CO_2R^d$, $(CH_2)_{1-4}C(=O)N(R^d)_2$, $C_2$–$C_8$ alkoxyalkyl, or fluorinated $C_2$–$C_8$ alkoxyalkyl;

each $R^6$ is a substituent connected to a ring atom other than $C(R^7R^8)$, spiro substituted carbon, or N and is independently hydrogen or $C_1$–$C_4$ alkyl;

$R^7$ is hydrogen, cyano, hydroxy, $CO_2R^d$, $CON(R^d)_2$, aryl, or substituted aryl; wherein each of the substituents on substituted aryl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^8$ is aryl, substituted aryl, heteroaryl, or substituted heteroaryl; wherein each of the substituents on substituted aryl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{1-4}CO_2R^d$, $(CH_2)_{0-4}C(=O)N(R^d)_2$, $(CH_2)_{0-4}SO_2R^d$, $C_2$–$C_8$ alkoxyalkyl, or fluorinated $C_2$–$C_8$ alkoxyalkyl; and wherein each of the substitutents on substituted heteroaryl is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^{10}$ is hydrogen, $C_1$–$C_6$ alkyl, fluorinated $C_1$–$C_6$ alkyl, $C_3$–$C_8$ cycloalkyl, or fluorinated $C_3$–$C_8$ cycloalkyl;

$R^{12}$ is hydrogen or $C_1$–$C_4$ alkyl;

each $X^1$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

Y is $C(R^a)=C(R^b)$, $C(R^aR^b)$—$C(R^a)=C(R^b)$, $C(R^a)=C(R^b)$—$C(R^aR^b)$, $[C(R^aR^b)]_{1-3}$, or

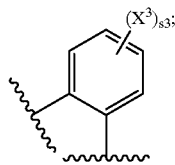

Z is absent, $C(R^aR^b)$, O, S, SO, $SO_2$, or $N(R^c)$; provided that (i) when Z is absent, Y is $C(R^a)=C(R^b)$, $C(R^aR^b)-C(R^a)=C(R^b)$, $C(R^a)=C(R^b)-C(R^aR^b)$, or

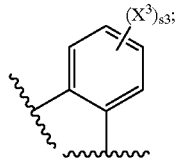

and (ii) when Z is $C(R^aR^b)$, O, S, SO, $SO_3$, or $N(R^c)$, Y is $[C(R^aR^b)]_{1-3}$ or

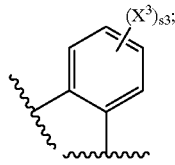

D is absent, $[C(R^aR^b)]_{1-4}$, $O[C(R^a)]_{1-2}$, $[C(R^a)]_{1-2}O$, $C(R^a)=C(R^b)$, $C(R^aR^b)-C(R^a)=C(R^b)$, or $C(R^a)=C(R^b)-C(R^aR^b)$;

E is absent, C(=O), C(=O)O, $N(SO_2R^c)C(R^aR^b)$, $N(R^c)C(=O)$, or $N(R^c)C(=O)O$, provided that (i) when E is absent, D is $[C(R^aR^b)]_{2-4}$, $O[C(R^aR^b)]_{1-2}$, $[C(R^aR^b)]_{1-2}O$, $C(R^a)=C(R^b)$, $C(R^aR^b)C(R^a)=C(R^b)$, or $C(R^a)=C(R^b)C(R^aR^b)$; (ii) when E is C(=O) or C(=O)O, D is $C(R^aR^b)$ or $C(R^aR^b)C(R^aR^b)$; and (iii) when E is $N(SO_2R^c)C(R^aR^b)$, $N(R^c)C(=O)$ or $N(R^c)C(=O)O$, D is absent or $C(R^aR^b)$;

each $X^2$ is independently hydrogen, halogen, cyano, $C_1-C_6$ alkyl, $C_3-C_8$ cycloalkyl, fluorinated $C_1-C_6$ alkyl, fluorinated $C_3-C_8$ cycloalkyl, $(CH_2)_{0-4}CO_2R^d$, $(CH_2)_{0-4}C(=O)N(R^d)_2$, $C_1-C_6$ alkoxy, fluorinated $C_1-C_6$ alkoxy, $C_2-C_8$ alkoxyalkyl, or fluorinated $C_2-C_8$ alkoxyalkyl;

each $X^3$ is independently hydrogen, halogen, cyano, $C_1-C_6$ alkyl, $C_3-C_8$ cycloalkyl, fluorinated $C_1-C_6$ alkyl, fluorinated $C_3-C_8$ cycloalkyl, $(CH_2)_{0-4}CO_2R^d$, $(CH_2)_{0-4}C(=O)N(R^d)_2$, $C_1-C_6$ alkoxy, fluorinated $C_1-C_6$ alkoxy, $C_2-C_8$ alkoxyalkyl, or fluorinated $C_2-C_8$ alkoxyalkyl;

$R^a$ and $R^b$ are each independently hydrogen, $C_1-C_4$ alkyl, and fluorinated $C_1-C_4$ alkyl;

$R^c$ is hydrogen, $C_1-C_4$ alkyl, or fluorinated $C_1-C_4$ alkyl;

$R^d$ is hydrogen, $C_1-C_6$ alkyl, or fluorinated $C_1-C_6$ alkyl;

m is an integer from 1 to 4;

p and q are each independently integers from 0 to 3;

s1 is an integer from 0 to 4;

s2 is an integer from 0 to 4;

s3 is an integer from 0 to 4; and t is an integer from 0 to 4;

and provided that when Q is of formula (a1), Z is O, Y is $[C(R^aR^b)]_{1-3}$, and $R^8$ is aryl, then $R^7$ is cyano, $CO_2R^d$, $CON(R^d)_2$, or substituted aryl;

or a pharmaceutically acceptable salt thereof.

2. The compound according to claim 1, wherein the compound is a (+)-enantiomer; or a pharmaceutically acceptable salt thereof.

3. The compound according to claim 1, wherein the compound is a (−)-enantiomer; or a pharmaceutically acceptable salt thereof.

4. The compound according to claim 1, wherein one of $R^1$ and $R^2$ is hydrogen or fluorine and the other of $R^1$ and $R^2$ is hydrogen, fluorine, $C_1-C_6$ alkyl, or $C_3-C_8$ cycloalkyl;

one of $R^3$ and $R^4$ is hydrogen or fluorine and the other of $R^3$ and $R^4$ is hydrogen, fluorine, $C_1-C_6$ alkyl, or $C_3-C_8$ cycloalkyl;

$R^5$ is hydrogen, $C_1-C_4$ alkyl, fluorinated $C_1-C_4$ alkyl, $C_3-C_6$ cycloalkyl, fluorinated $C_3-C_6$ cycloalkyl, $(CH_2)_{1-2}CO_2R^d$, $(CH_2)_{1-2}C(=O)N(R^d)_2$, $C_2-C_8$ alkoxyalkyl, or fluorinated $C_2-C_8$ alkoxyalkyl;

$R^7$ is hydrogen, cyano, hydroxy, $CO_2R^d$, $CON(R^d)_2$, phenyl, or mono- or di- or tri-substituted phenyl;

$R^8$ is phenyl, naphthyl, pyridyl, pyrazinyl, thienyl, furanyl, or mono- or di- or tri-substituted phenyl, naphthyl, pyridyl, pyrazinyl, thienyl, or furanyl;

$R^d$ is hydrogen, $C_1-C_4$ alkyl, or $(CH_2)_{0-4}CF_3$;

m is an integer from 1 to 3;

p and q are each integers from 0 to 3, provided that the sum of p and q is an integer less than or equal to 3;

s1 is an integer from 0 to 3;

s2 is an integer from 0 to 2;

s3 is an integer from 0 to 2; and t is an integer from 0 to 2;

and provided that when Q is of formula (a1), Z is O, Y is $[C(R^aR^b)]_{1-3}$, and $R^8$ is phenyl, then $R^7$ is cyano, $CO_2R^d$, $CON(R^d)_2$, or mono- or di- or tri-substituted phenyl;

or a pharmaceutically acceptable salt thereof.

5. The compound according to claim 4, wherein Q is

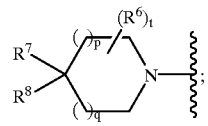

and provided that when Z is O, Y is $[C(R^aR^b)]_{1-3}$, and $R^8$ is phenyl, then $R^7$ is cyano, $CO_2R^d$, $CON(R^d)_2$, or mono- or di- or tri-substituted phenyl;

or a pharmaceutically acceptable salt thereof.

6. The compound according to claim 5, having the formula

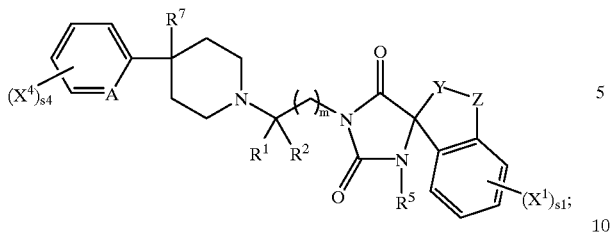

wherein

A is N or $CX^4$;

one of $R^1$ and $R^2$ is hydrogen and the other of $R^1$ and $R^2$ is hydrogen, methyl, or ethyl;

$R^5$ is hydrogen, methyl, ethyl, $CH_2OCH_3$, $CH_2OCH_2CH_3$, $CH_2CO_2CH_3$, or $CH_2CO_2CH_2CH_3$;

$R^7$ is hydrogen, hydroxy, cyano, $CO_2R^d$, $CON(R^d)_2$, phenyl, or mono- or di-substituted phenyl; wherein each of the substituents on substituted phenyl is independently halogen, cyano, hydroxy, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

Y is $C(R^a)=C(R^b)$, $[C(R^aR^b)]_{1-3}$, or

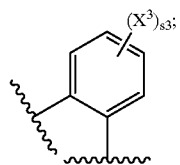

Z is absent, $C(R^aR^b)$, O, S, SO, $SO_2$, or $N(R^c)$; provided that (i) when Z is absent, Y is $C(R^a)=C(R^b)$ or

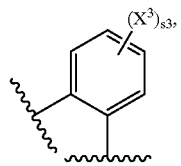

and (ii) when Z is $C(R^aR^b)$, O, S, SO, $SO_2$, or $N(R^c)$, Y is $[C(R^aR^b)]_{1-3}$;

each $X^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^4$ is independently hydrogen, halogen, cyano, $C_1$–$C_4$ alkyl, $(CH_2)0$-$4CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^d$ is hydrogen, methyl, ethyl, or $CF_3$;

m is an integer equal to 2 or 3; and s4 is an integer from 0 to 3;

and provided that when Z is O and

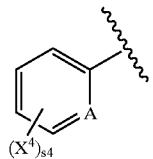

is phenyl, then $R^7$ is cyano, $CO_2R^d$, $CON(R^d)_2$, or mono- or di- or tri-substituted phenyl;

or a pharmaceutically acceptable salt thereof.

7. The compound according to claim 6, wherein the compound is 1-{3-[4-(4-fluorophenyl)piperidin-1-yl]butyl}-5'-chloro-spiro[imidazolidine-4,1'indan]-2,5-dione or a pharmaceutically acceptable salt thereof.

8. The compound according to claim 6, having the formula

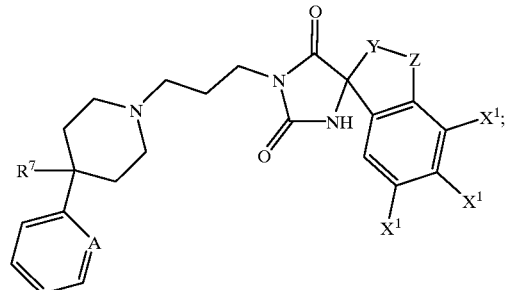

wherein $R^7$ is hydrogen or cyano;

Y is CH=CH, $(CH_2)_{1-3}$, or

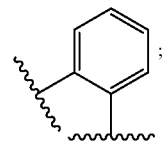

Z is absent, $CH_2$, O, S, SO, or $SO_2$; provided that (i) when Z is absent, Y is CH=CH or

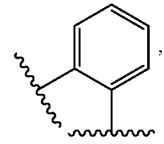

and (ii) when Z is $CH_2$, O, S, SO, or $SO_2$, Y is $(CH_2)_{1-3}$;

each $X^1$ is independently hydrogen, fluorine, chlorine, cyano, methyl, ethyl, methoxy, ethoxy, $CF_3$, or $OCF_3$; and each $X^4$ is independently hydrogen, fluorine, chlorine, cyano, methyl, ethyl, methoxy, ethoxy, $CF_3$, or $OCF_3$;

and provided that when Z is O and

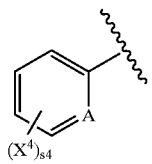

is phenyl, then R⁷ is cyano;
or a pharmaceutically acceptable salt thereof.

9. The compound according to claim 8, wherein the compound is selected from the group consisting of (+/−)-1-{3-[4-(2-cyano-4-fluorophenyl)piperidin-1-yl]propyl}-5'-spiro[imidazolidine-4,1'indan]-2,5-dione;

(+)-1-{3-[4-(2-cyano-4-fluorophenyl)piperidin-1-yl]propyl}-5'-fluoro-spiro[imidazolidine-4,1'indan]-2,5-dione;

(−)-1-{3-[4-(2-cyano-4-fluorophenyl)piperidin-1-yl]propy}-5-fluoro-spiro[imidazolidine-4,1'indan]-2,5-dione;

(+/−)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione;

(+)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione;

(−)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione;

(+/−)-1-{3-[4-(4-fluorophenyl)piperidin-1-yl]propyl}-5'-fluoro-spiro[imidazolidine-4,1'indan]-2,5-dione;

(+/−)-1-{3-[4-cyano-4-phenyl-piperidin-1-yl]propyl}-5'-fluoro-spiro[imidazolidine-4,1'indan]-2,5-dione;

(+)-1-{3-[4-cyano-4-phenyl-piperidin-1-yl]propyl}-5'-fluoro-spiro[imidazolidine-4,1'indan]-2,5-dione;

(−)-1-{3-[4-cyano-4-phenyl-piperidin-1-yl]propyl}-5'-fluoro-spiro[imidazolidine-4,1'indan]-2,5-dione;

(+/−)-1-{3-[4-(4-cyano-4-(2-cyanophenyl))piperidin-1-yl]propyl}-5'-fluoro-spiro[imidazolidine-4,1'indan]-2,5-dione;

(+/−)-1-{3-[4-cyano-4-phenyl-piperidin-1-yl]propyl}-6'-fluoro-spiro[imidazolidine-4,1'indan]-2,5-dione;

(+/−)-1-{3-[4-(4-fluoro-2-cyanophenyl)piperidin-1-yl]propyl}-5',6'-difluoro-spiro[imidazolidine-4,1'indan]-2,5-dione;

(+)-1-{3-[4-(4-fluoro-2-cyanophenyl)piperidin-1-yl]propyl}-5',6'-difluoro-spiro[imidazolidine-4,1'indan]-2,5-dione;

(−)-1-{3-[4-(4-fluoro-2-cyanophenyl)piperidin-1-yl]propyl}-5',6'-difluoro-spiro[imidazolidine-4,1'indan]-2,5-dione; (+/−)-1-{3-[4-(4-fluorophenyl)piperidin-1-yl]propyl}-5'-chloro-spiro[imidazolidine-4,1'indan]-2,5-dione;

(+/−)-1-{3-[4-(4-fluoro-2-cyanophenyl)piperidin-1-yl]propyl}-5'-chloro-spiro[imidazolidine-4,1'indan]-2,5-dione;

(+)-1-{3-[4-(4-fluoro-2-cyanophenyl)piperidin-1-yl]propyl}-5'-chloro-spiro[imidazolidine-4,1'indan]-2,5-dione;

(−)-1-{3-[4-(4-fluoro-2-cyanophenyl)piperidin-1-yl]propyl}-5'-chloro-spiro[inidazolidine-4,1'indan]-2,5-dione;

(+/−)-1-{3-[4-(2-pyridinyl)piperidin-1-yl]propyl}-5'-chloro-spiro[imidazolidine-4,1'indan]-2,5-dione;

(+/−)-1-{3-[4-(4-fluoro-2-cyanophenyl)piperidin-1-yl]propyl}-5'-methyl-spiro[imidazolidine-4,1'indan]-2,5-dione;

(+)-1-{3-[4-(4-fluoro-2-cyanophenyl)piperidin-1-yl]propyl}-5'-methyl-spiro[imidazolidine4,1'indan]-2,5-dione;

(−)-1-{3-[4-(4-fluoro-2-cyanophenyl)piperidin-1-yl]propyl}-5'-methyl-spiro[imidazolidine-4,1'indan]-2,5-dione;

(+/−)-1-{3-[4-cyano-4-phenyl-piperidin-1-yl]propyl}-3-fluoro-spiro[9H-fluorene-9,4'-imidazolidine]-2',5'-dione;

(+/−)-1'-{3-[4-(4-fluorophenyl)piperidin-1-yl]propyl}-7-fluoro-2,3-dihydro-spiro[4H-1-benzopyran-4,4'-imidazolidine]-2',5'-dione;

(+)-1'-{3-[4-(4-fluorophenyl)piperidin-1-yl]propyl}-7-fluoro-2,3-dihydro-spiro[4H-1-benzopyran-4,4'-imidazolidine]-2',5'-dione;

(−)-1'-{3-[4-(4-fluorophenyl)piperidin-1-yl]propyl}-7-fluoro-2,3-dihydro-spiro[4H-1-benzopyran-4,4'-imidazolidine]-2',5'-dione;

(+/−)-1'-{3-[4-(4-fluoro-2-cyanophenyl)piperidin-1-yl]propyl}-7-chloro-2,3-dihydro-spiro[4H-1-benzopyran-4,4'-imidazolidine]-2',5'-dione;

(+/−)-1'-{3-[4-(4-fluoro-2-cyano-phenyl)piperidin-1-yl]propyl}-7-fluoro-2,3-dihydro-spiro[4H-1-benzothiopyran-4,4'-imidazolidine]-2',5'-dione;

(+/−)-1'-{3-[4-(4-fluoro-2-cyano-phenyl)piperidin-1-yl]propyl}-7-fluoro-2,3-dihydro-1,1-dioxo-spiro[4H-1-benzothio-pyran-4,4'-imidazolidine]-2',5'-dione;

(+/−)-1'-[3-(4-cyano-4-phenylpiperidin-1-yl)propyl]-6-fluoro-2,3-dihydro-spiro[4H-1-benzopyran-4,4'-imidazolidine]-2',5'-dione;

(+/−)-1'-[3-(4-cyano-4-phenylpiperidin-1-yl)propyl]-3-fluoro-6,7,8,9-tetrahydro-spiro[5H-benzocycloheptene-5,4'-imidazolidine]-2',5'-dione;

(+/−)-1'-{3-[4-(4-fluoro-2-cyano-phenyl)piperidin-1-yl]propyl}-6-fluoro-2,3-dihydro-spiro[1-benzofuran-3(2H),4'-imidazolidine]-2',5'-dione;

(+/−)-1'-{3-[4-(4-fluoro-2-cyano-phenyl)piperidin-1-yl]propyl}-8-fluoro-2,3,4,5-tetrahydro-spiro[1-benzoxepin-5(2H),4'-imidazolidine]-2',5'-dione;

and pharmaceutically acceptable salts thereof.

10. The compound according to claim 9, wherein the compound is selected from the group consisting of (+)-1-{3-[4-(2-cyano-4-fluorophenyl)piperidin-1-yl]propyl}-5'-fluoro-spiro[imidazolidine-4,1'indan]-2,5-dione;

(+)-1'-{3-[4-(4-fluoro-2-cyanophenyl)piperidin-1-yl]propyl}-7-fluoro-2,3-dihydro-spiro[4H-1-benzopyran-4,4'-imidazolidine]-2',5'-dione;

and pharmaceutically acceptable salts thereof.

11. The compound according to claim 4, wherein Q is

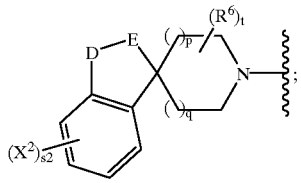

or a pharmaceutically acceptable salt thereof.

12. The compound according to claim 11, having the formula

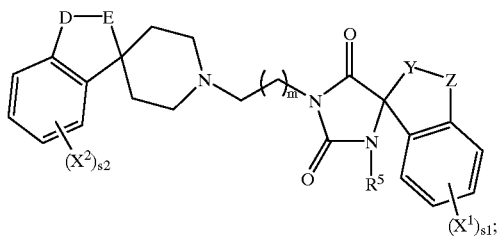

wherein
R⁵ is hydrogen, methyl, or ethyl;
Y is $C(R^a)=C(R^b)$, $[C(R^aR^b)]_{1-3}$, or

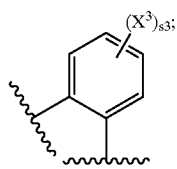

Z is absent, $C(R^aR^b)$, O, S, SO, SO$_2$, or N(R$^c$); provided that (i) when Z is absent, Y is $C(R^a)=C(R^b)$ or

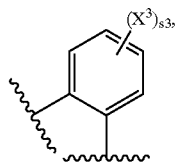

and (ii) when Z is $C(R^aR^b)$, O, S, SO, SO$_2$, or N(R$^c$), Y is $[C(R^aR^b)]_{1-3}$;
each X¹ is independently hydrogen, halogen, cyano, $C_1$–$C_4$ alkyl, $(CH_2)_{0-4}CF_3$, $C_1$–$C_4$ alkoxy, OCF$_3$, $(CH_2)_{0-4}CO_2R^d$, $(CH_2)_{1-4}OCH_3$, or $(CH_2)_{1-4}OCF_3$;
each X² is independently hydrogen, halogen, cyano, $C_1$–$C_4$ alkyl, $(CH_2)_{0-4}CF_3$, $C_1$–$C_4$ alkoxy, OCF$_3$, $(CH_2)_{0-4}CO_2R^d$, $(CH_2)_{1-4}OCH_3$, or $(CH_2)_{1-4}OCF_3$;
each X³ is independently hydrogen, halogen, cyano, $C_1$–$C_4$ alkyl, $(CH_2)_{0-4}CF_3$, $C_1$–$C_4$ alkoxy, OCF$_3$, $(CH_2)_{0-4}CO_2R^d$, $(CH_2)_{1-4}OCH_3$, or $(CH_2)_{1-4}OCF_3$;
R$^d$ is hydrogen, methyl, ethyl, or CF$_3$; and
m is an integer equal to 2 or 3;
or a pharmaceutically acceptable salt thereof.

13. The compound according to claim 12, having the formula

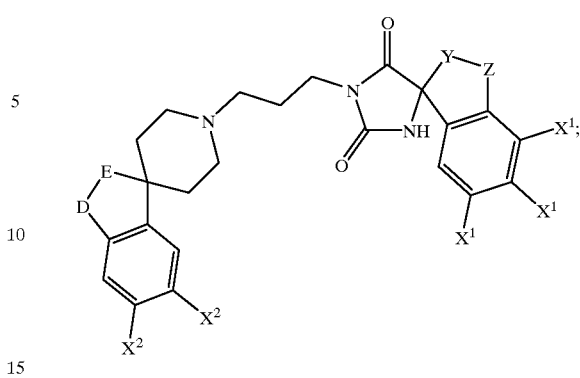

wherein
Y is CH=CH, $(CH_2)_{1-3}$, or

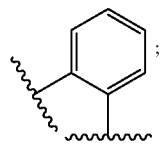

Z is absent, CH$_2$, O, S, SO, or SO$_2$; provided that (i) when Z is absent, Y is CH=CH or

and (ii) when Z is CH$_2$, O, S, SO, or SO$_2$, Y is $(CH_2)_{1-3}$;
each X¹ is independently hydrogen, fluorine, chlorine, cyano, methyl, ethyl, methoxy, ethoxy, CF$_3$, or OCF$_3$; and
each X² is independently hydrogen, fluorine, chlorine, cyano, methyl, ethyl, methoxy, ethoxy, CF$_3$, or OCF$_3$;
or a pharmaceutically acceptable salt thereof.

14. The compound according to claim 13, wherein the compound is selected from the group consisting of
(+/−)-1-{3-{spiro[indano-1,4'-piperidin]-1-yl}propyl}-5'-fluoro-spiro[imidazolidine-4,1'indan]-2,5-dione;
(+)-1-{3-{spiro[indano-1,4'-piperidin]-1-yl}propyl}-5'-fluoro-spiro[imidazolidine-4,1'indan]-2,5-dione;
(−)-1-{3-{spiro[indano-1,4'-piperidin]-1-yl}propyl}-5'-fluoro-spiro[imidazoline-4,1'indan]-2,5-dione;
(+/−)-1-{3-{6-chlorospiro[4H-3,1-benzoxazine-4,4'-piperidin]-2(1H)-on-1'-yl}propyl}-5'-fluoro-spiro[imidazolidine-4,1'indan]-2,5-dione;
(+/−)-1-{3-{spiro[indano-1,4'-piperidine]-1-yl}propyl}-6'-fluoro-spiro[imidazoline-4,1'indan]-2,5-dione;
(+/−)-1-{3-{spiro[indano-1,4'-piperidin]-1-yl}propyl}-5',6'-difluoro-spiro[imidazolidine4,1'indan]-2,5-dione;
(+/−)-1-{3-{spiro[indano-1,4'-piperidin]-1-yl}propyl}-5'-chloro-spiro[imidazolidine-4,1'indan]-2,5-dione;
(+)-1-{3-{spiro[indano-1,4'-piperidin]-1-yl}propyl}5'-chloro-spiro[imidazolidine-4,1'indan]-2,5-dione;
(−)-1-{3-{spiro[indano-1,4'-piperidin]-1-yl}propyl}-5'-chloro-spiro[imidazolidine-4,1'indan]-2,5-dione;
(+/−)-1-{3-{6-chlorospiro[4H-3,1-benzoxazine-4,4'-piperidin]-2(1H)-on-1'-yl}propyl}-5'-chloro-spiro[imidazolidine-4,1'indan]-2,5-dione;

(+-)-1-{3-{spiro[indano-1,4'-piperidin]-1-yl}propyl}-6'-chloro-spiro[imidazolidine-4,1'indan]-2,5-dione;

(+/−)-1-{3-{spiro[indano-1,4'-piperidin]-1-yl}propyl}4'-methyl-spiro[imidazolidine-4,1'indan]-2,5-dione;

(+/−)-1-{3-{spiro[indano-1,4'-piperidin]-1-yl}propyl}-5'-methyl-spiro[imidazoline-4,1'indan]-2,5-dione;

(+)-1-{3-{spiro[indano-1,4'-piperidin]-1-yl}propyl}5'-methyl-spiro[imidazolidine-4,1'indan]-2,5-dione;

(−)-1-{3-{spiro[indano-1,4'-piperidin]-1-yl}propyl}-5'-methyl-spiro[imidazolidine-4,1'indan]-2,5-dione;

(+/−)-1-{3-{spiro[indano-1,4'-piperidin]-1-yl}propyl}-6'-methyl-spiro[imidazolidine-4,1'indan]-2,5-dione;

and pharmaceutically acceptable salts thereof.

15. A pharmaceutical composition comprising a therapeutically effective amount of the compound according to claim 1 and a pharmaceutically acceptable carrier.

16. A process for making a pharmaceutical composition comprising combining a therapeutically effective amount of the compound according to claim 1 and a pharmaceutically acceptable carrier.

17. The composition according to claim 15 further comprising a therapeutically effective amount of a testosterone 5-alpha reductase inhibitor.

18. The composition according to claim 17, wherein the testosterone 5-alpha reductase inhibitor is a type 1, a type 2, both a type 1 and a type 2, or a dual type 1 and type 2 testosterone 5-alpha reductase inhibitor.

19. The composition according to claim 18, wherein the testosterone 5-alpha reductase inhibitor is a type 2 testosterone 5-alpha reductase inhibitor.

20. The composition according to claim 19, wherein the testosterone 5-alpha reductase inhibitor is finasteride.

21. A method of treating benign prostatic hyperplasia in a subject in need thereof which comprises administering to the subject a therapeutically effective amount of the compound according to claim 1.

22. The method according to claim 21, wherein the compound does not cause a fall in blood pressure at dosages effective to alleviate benign prostatic hyperlasia.

23. The method according to claim 21, wherein the compound is administered in combination with a therapeutically effective amount of a testosterone 5-alpha reductase inhibitor.

24. The method according to claim 23, wherein the testosterone 5-alpha reductase inhibitor is finasteride.

25. A method of treating benign prostatic hyperplasia in a subject in need thereof which comprises administering a therapeutically effective amount of the composition according to claim 15.

26. The method according to claim 25, wherein the composition further comprises a therapeutically effective amount of a testosterone 5-alpha reductase inhibitor.

27. A method of relaxing lower urinary tract tissue in a subject in need thereof which comprises administering to the subject a therapeutically effective amount of the compound according to claim 1.

28. The method according to claim 27, wherein the compound is administered in combination with a therapeutically effective amount of a testosterone 5-alpha reductase inhibitor.

29. The method according to claim 28, wherein the testosterone 5-alpha reductase inhibitor is finasteride.

30. A method of eliciting an alpha 1a antagonizing effect in a mammal in need thereof, comprising administering to the mammal a therapeutically effective amount of the compound according to claim 1.

* * * * *